(12) United States Patent
Nichols

(10) Patent No.: US 12,649,779 B2
(45) Date of Patent: Jun. 9, 2026

---

(54) AMYLOID-BETA ANTIBODIES

(71) Applicant: The Curators of the University of Missouri, Columbia, MO (US)

(72) Inventor: Michael R. Nichols, St. Charles, MO (US)

(73) Assignee: The Curators of the University of Missouri, Columbia, MO (US)

( * ) Notice: Subject to any disclaimer, the term of this patent is extended or adjusted under 35 U.S.C. 154(b) by 1145 days.

(21) Appl. No.: 17/636,923

(22) PCT Filed: Aug. 20, 2020

(86) PCT No.: PCT/US2020/047163
§ 371 (c)(1),
(2) Date: Feb. 21, 2022

(87) PCT Pub. No.: WO2021/035033
PCT Pub. Date: Feb. 25, 2021

(65) Prior Publication Data
US 2022/0356233 A1      Nov. 10, 2022

Related U.S. Application Data

(60) Provisional application No. 62/889,220, filed on Aug. 20, 2019.

(51) Int. Cl.
*C07K 16/18* (2006.01)
*A61P 25/28* (2006.01)

(52) U.S. Cl.
CPC .............. *C07K 16/18* (2013.01); *A61P 25/28* (2018.01); *C07K 2317/34* (2013.01); *C07K 2317/92* (2013.01)

(58) Field of Classification Search
CPC ................ C07K 16/18; C07K 2317/34; C07K 2317/56; C07K 2317/92; A61P 25/28; A61K 39/3955; A61K 2039/505
See application file for complete search history.

(56) References Cited

U.S. PATENT DOCUMENTS

| | | | | |
|---|---|---|---|---|
| 10,035,847 | B2 * | 7/2018 | Graham | ............. C07K 14/4711 |
| 2016/0319006 | A1 * | 11/2016 | Ravetch | ................... A61P 25/00 |
| 2019/0119365 | A1 | 4/2019 | Baurin et al. | |
| 2019/0389942 | A1 * | 12/2019 | Taupin | .................... A61P 25/28 |

FOREIGN PATENT DOCUMENTS

WO         2010006214 A1      1/2010

OTHER PUBLICATIONS

Edwards et al. J. Mol. Biol. 2003, 334:103-118. (Year: 2003).*
Lloyd et al. Protein Eng. Design & Select, 2009, 22(3):159-168. (Year: 2009).*

Colvin et al., The conformational epitope for a new Abeta42 protofibril-selective antibody partially overlaps with peptide N-terminal region; Journal of Neurocheimistry; 2017, vol. 143, pp. 736-749.
Georganopoulou et al., Nanoparticle-Based Detection in Cerebral Spinal Fluid of a Soluble Pathogenic Biomarker for Alzheimer's Disease; Proceedings of the National Academy of Sciences of the United States of America , Feb. 15, 2005, vol. 102, No. 7 (Feb. 15, 2005), pp. 2273-2276.
Gong et al., Alzheimer's Disease-Affected Brain: Presence of Oligomeric Aβ Ligands (ADDLs) Suggests a Molecular Basis for Reversible Memory Loss; Proceedings of the National Academy of Sciences of the United States of America , Sep. 2, 2003, vol. 100, No. 18 (Sep. 2, 2003), pp. 10417-10422.
Haass et al., Soluble protein oligomers in neurodegeneration: lessons from Alzheimer's amyloid Beta-peptide; Mechanisms of Disease; Nature Reviews: Molecular Cell Biology, 2007, vol. 8, 12-pages.
Hardy, Amyloid, the presenilins and Alzheimer's disease; Trends Neurosci., 1997, vol. 20, pp. 154-159.
Harper et al., Observation of metastable A-beta amyloid protofibrils by atomic force microscopy; Research Paper; Chemistry and Biology, 1997, vol. I 4, pp. 119-125.
Harper et al., Assembly of A-beta Amyloid Protofibrils: An in Vitro Model for a Possible Early Event in Alzheimer's Disease; Biochemistry, 1999, vol. 38, pp. 8972-8980.
Jan et al., Preparation and characterization of toxic A-beta aggregates for structural and functional studies In Alzheimer's disease research; Nature Protocols; 2010, vol. 5, No. 6, 28-pages.
Jarrett et al., The Carboxy Terminus of the Beta Amyloid Protein Is Critical for the Seeing of Amyloid Formation: Implications for the Pathogenesis of Alzheimer's Disease:The American Chemical Society; 1993, vol. 32, No. 18, 5-pages.
Kayed et al., Common Structure of Soluble Amyloid Oligomers Implies Common Mechanism of Pathogenesis; Science , Apr. 18, 2003, New Series, vol. 300, No. 5618 (Apr. 18, 2003), pp. 486-489.
Kheterpal et al., A-beta Protofibrils Possess a Stable Core Structure Resistant to Hydrogen Exhange; Biochemistry; 2003, vol. 41, pp. 14092-14098.
Koffie et al., Oligomeric Amyloid B Associates with Postsynaptic Densities and Correlates with Excitatory Synapse Loss Near Senile Plaques; Proceedings of the National Academy of Sciences of the United States of America , Mar. 10, 2009, vol. 106, No. 10 (Mar. 10, 2009), pp. 4012-4017.
Ambert et al., Diffusible, Nonfibrillar Ligands Derived from Aβ 1-42 are Potent Central Nervous System Neurotoxins; Proceedings of the National Academy of Sciences of the United States of America , May 26, 1998, vol. 95, No. 11 (May 26, 1998), pp. 6448-6453.
Ma et al., Overview of the detection methods for equilibrium dissociation constan Kd of drug-receptor interaction; Journal of Pharmaceutical Analysis; 2018, vol. 8, pp. 147-152.

(Continued)

*Primary Examiner* — Kimberly Ballard
(74) *Attorney, Agent, or Firm* — Brownstein Hyatt Farber Schreck, LLP

(57) ABSTRACT

Provided herein are antibodies selective for Aβ protofibrils, compositions containing the antibodies and methods of using the antibodies.

5 Claims, 15 Drawing Sheets

Specification includes a Sequence Listing.

(56)                    References Cited

OTHER PUBLICATIONS

Nichols et al., Biophysical Comparison of Soluble Amyloid-Beta(1-42) Protofibrils, Oligomers, and Protofilaments; Biochemistry, 2015, vol. 54, pp. 2193-2204.

O'Nuallain et al., Amyloid Beta-Protein Dimers Rapidly Form Stable Synaptotoxic Protofibrils; The Journal of Neuroscience, 2010, vol. 30, No. 43, pp. 14411-14419.

Paranjape et al., Isolated anyloid-Beta(1-42) Protofibrils, But Not Isolated Fibrils, Are Robust Stimulators of Microglia; ACS Chemical, Neuroscience; 2012; vol. 3, pp. 302-311.

Glenner et al., Alzheimer's Disease: Initial Report of the Purification and Characterizationf a Novel Cerebrovascular Amyloid Protein; Biochemical and Biophyisical Research Communications; 1984, vol. 120, No. 3, 6-pages.

Gravina et al., Amyloid Beta Protein (Abeta) in Alzheimer's Disease Brain; The Journal of Biological Chemistry; 1995, vol. 270, No. 1, pp. 7013-7016.

Selkoe et al., Cell biology of protein misfolding: The examples of Alzheimer's and Parkinson's diseases; Nature Cell Biology, 2004, vol. 6, No. 11, 8-pages.

Suzuki et al., An Increased Percentage of Long Amyloid B Protein Secreted by Familial Amyloid β Protein Precursor (βAPP717) Mutants; May 27, 1994, New Series, vol. 264, No. 5163 (May 27, 1994), pp. 1336-1340.

Terry et al., Ultrastructural Studies in Alzheimer's Presenile Dementia; The Department of Pathology (Neuropathology), 1964, vol. 44, No. 2, 29-pages.

Walsh et al., Amyloid Beta-Protein Fibrillogenesis; The Journal of Biological Chemistry; 1997, vol. 272, No. 35, pp. 22364-22372.

Walsh et al., Amyloid Beta-Protein Fibrillogenesis; The Journal of Biological Chemistry; 1999, vol. 274, No. 36, pp. 25945-25952.

Walsh et al., Naturally secreted oligomers fo amyloid Beta protein potently inhibit hippocampal long-term potentiation in vivo; Nature, 2002, vol. 416, 6-pages.

Walsh et al., Abeta Oligomers—a decade of discovery; Journal of Neurochemistry, 2007, vol. 101, pp. 1172-1184.

Westerman et al., The Relationship between A-beta and Memory in the Tg2576 Mouse Model of Alzheimer's Disease; The Journal of Neuroscience, 2002, vol. 22, No. 5, pp. 1858, 1867.

Ye et al., Protofibrils of amyloid Beta-protein inhibit specific K+ currents in neocortical cultures; Neurobiology of Disease, 2003, 28-pages.

* cited by examiner

Aβ monomers      Aβ protofibrils      Aβ fibrils

**Cloning
(heavy chain & light chain variable regions)**

Transformation/Colony Growth

Colony PCR

DNA Prep

Sequencing

HC/LC Co-transfection & Expression

AMYLOID-BETA ANTIBODIES

CROSS-REFERENCE TO RELATED APPLICATIONS

This application claims priority to International Application Number PCT/US2020/047163, filed on Aug. 20, 2020, which claims benefit of U.S. Provisional Patent Application Ser. No. 62/889,220, filed on Aug. 20, 2019, the disclosures of which are hereby expressly incorporated by reference in their entireties.

INCORPORATION OF SEQUENCE LISTING

A paper copy of the Sequence Listing and a computer readable form of the Sequence Listing containing the file named "UMSL16002.WO2_ST25.txt", which is 34,725 bytes in size (as measured in MICROSOFT WINDOWS® EXPLORER), are provided herein and are herein incorporated by reference. This Sequence Listing consists of SEQ ID NOS: 1-37.

FIELD OF THE INVENTION

Provided herein are antibodies and antigen-binding fragments thereof that bind amyloid-beta (Aβ) protofibrils. Also provided are pharmaceutical compositions and methods of using the provided antibodies to diagnose or treat Alzheimer's Disease or other conditions associated with aggregation of Aβ.

BACKGROUND OF THE INVENTION

Alzheimer's disease (AD) is a progressive neurodegenerative illness diagnosed clinically by dementia and pathologically by the presence of senile plaques and neurofibrillary tangles in the brain (1, 2). The primary component of the plaques is Aβ (3), a 40- or 42-amino acid peptide, which is derived from proteolysis of the amyloid precursor protein (APP) (4). A large body of evidence supports a principal role for Aβ in AD etiology. The strongest argument for the role of Aβ in AD comes from genetic studies of families that exhibit early-onset familial AD (FAD). These studies have identified a number of nucleotide mutations closely linked to Aβ (5) that either increase Aβ levels or increase the propensity for Aβ aggregation. Many of the genetic mutations that cause FAD increase the ratio of Aβ42 relative to Aβ40. The additional two hydrophobic amino acid residues on Aβ42 give the peptide a significantly increased propensity for aggregation (6) and explains the observation that plaques consist overwhelmingly of Aβ42 (7).

Amyloid fibrils can be found in many human neurodegenerative diseases including Alzheimer's, Parkinson's, and priori diseases (2). Aβ is the most widely studied amyloid fibril-forming protein. Numerous in vitro studies have shown that Aβ monomer will undergo non-covalent self-assembly (6) to form a polydisperse mixture of soluble oligomers (8,9) and protofibrils (10-12) with high β-sheet content (13) and ultimately insoluble fibrils (14).

Difficulties have been encountered trying to correlate insoluble fibrillar Aβ with memory loss in a transgenic mouse model (15). This eventually caused the research field to shift their investigative focus to soluble Aβ aggregates as toxic agents in AD (16,17). Numerous oligomeric species have been characterized including globular prefibrillar oligomers (8, 9) and protofibrils (10-12). These diffusible oligomeric species are potent neurotoxins (18) and are present in the human AD brain (19) and cerebrospinal fluid (CSF) (20). Even senile plaques, which contain fibrillar Aβ at the core (21), are surrounded by a halo of oligomeric Aβ as recently shown by Hyman and colleagues by immunostaining with NAB61 antibody (22).

Aβ protofibrils are small soluble fibril precursors that possess significant β-sheet structure (10, 13, 23). Protofibrils have similarities to fibrils based on thioflavin T binding, circular dichroism (13) and hydrogen exchange (24), but have not yet developed the full stability or size of fibrillar Aβ (13, 23, 24). Protofibrils display toxicity to neurons (13), disrupt ion channels (25), inhibit hippocampal long-term potentiation (26), and are potent proinflammatory stimuli (27). Disruption or clearance of protofibrils has promising therapeutic potential (28).

There is a need, therefore, for specific antibodies that can target Aβ protofibrils and aid in their clearance (FIG. 1). These antibodies may be useful in diagnosing, monitoring or treating conditions associated with amyloid aggregation.

BRIEF SUMMARY OF THE INVENTION

An antibody or antigen-binding fragment thereof is provided. The antibody or antigen-binding fragment has selectivity for Aβ protofibrils and comprises (a) an immunoglobulin heavy chain variable region comprising at least 70% sequence identity to any one of SEQ ID NOs: 1, 3, 5, 7, 10, 32, 34, 12, and 14; and/or (b) an immunoglobulin light chain variable region comprising at least 70% sequence identity to any one of SEQ ID NOs: 2, 4, 6, 8, 9, 11, 33, 13, and 15.

Further provided are nucleic acids comprising a nucleotide sequence encoding an immunoglobulin light chain variable region and/or an immunoglobulin heavy chain variable region of any antibody or antigen-binding fragment provided herein. Also provided are expression vectors comprising the nucleic acids, host cells comprising the expression vectors, and methods of producing the antibodies and antigen-binding fragments.

Also provided are pharmaceutical compositions comprising an antibody or antigen-binding fragment described herein and a pharmaceutically acceptable carrier.

Also provided is a method for measuring an amount of Aβ protofibrils and/or aggregated Aβ protein in a subject. The method comprises contacting a tissue or body fluid in the subject or obtained from the subject with an antibody or antigen-binding fragment thereof as described herein and measuring the amount of antibody or antigen-binding fragment bound to the Aβ protofibrils and/or aggregated Aβ protein.

Further provided is a method of reducing an amount of Aβ protofibrils in a subject. The method comprises administering to the subject a therapeutically effective amount of the antibody or antigen-binding fragment thereof as described herein.

Also provided is a method of treatment and/or prophylaxis of Alzheimer's disease or another disease associated with amyloid protofibril aggregation in a subject having, or being at risk of developing said disease or disorder. The method comprises administering to the subject a therapeutically effective amount of the antibody or antigen-binding fragment thereof as described herein.

Other objects and features will be in part apparent and in part pointed out hereinafter.

DETAILED DESCRIPTION OF THE INVENTION

Figure 1:
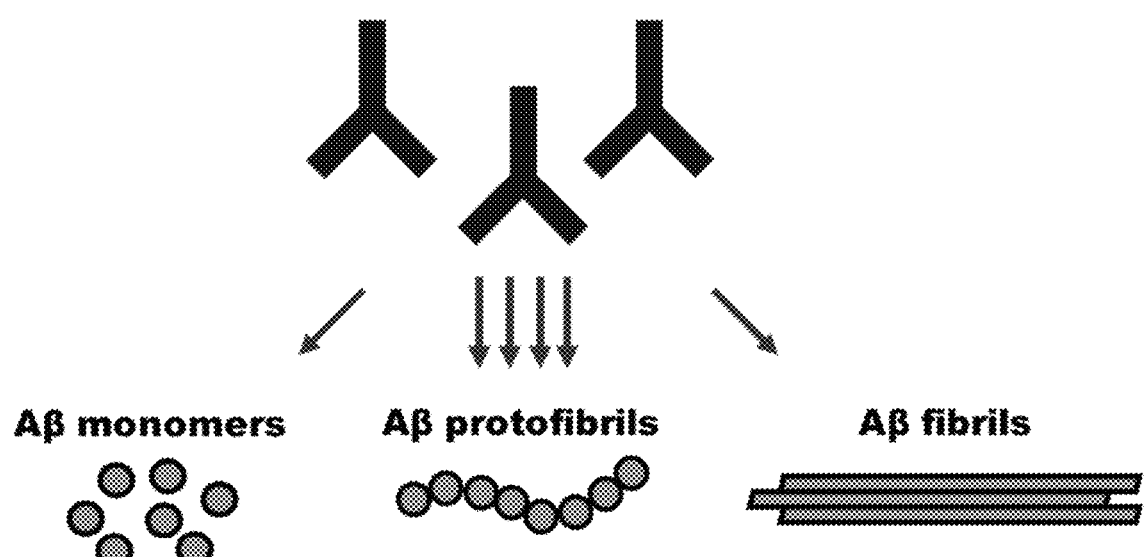
FIG. 1. Schematic of the antibodies described herein, illustrating their preference for Aβ protofibrils over Aβ monomers or Aβ fibrils.
Figure 2:
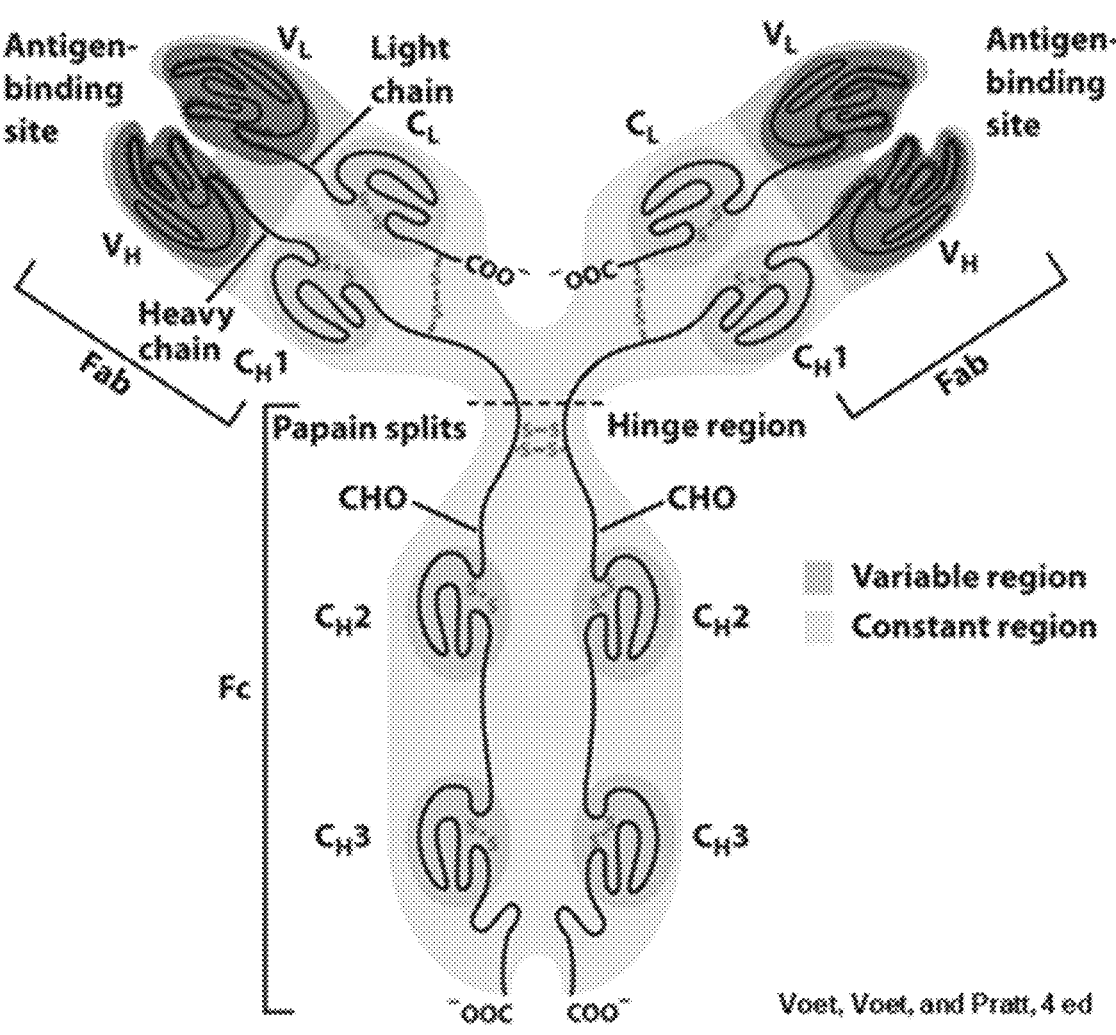
FIG. 2. Diagram of an IgG antibody with variable and constant regions indicated.

Provided herein are antibodies and antigen-binding fragments thereof that that bind Aβ protofibrils, with little to no selectivity for Aβ monomers or fibrils. The unique conformational specificity of these antibodies enables their use as important diagnostic and/or monitoring tools that can enable the tracking of various diseases or conditions associated with abnormal protein aggregation. The antibodies or antigen-binding fragments thereof comprise (a) an immunoglobulin heavy chain variable region comprising at least 70% sequence identity to any one of SEQ ID NOs: 1, 3, 5, 7, 10, 32, 34, 12 and 14; and/or (b) an immunoglobulin light chain variable region comprising at least 70% sequence identity to any one of SEQ ID NOs: 2, 4, 6, 8, 9, 11, 33, 13 and 15. Specific light and heavy chains of the antibodies provided herein are described in more detail below.
Antibody Structure and Sequences Thereof The general structure of an IgG antibody is shown in FIG. 2. Briefly, there are two major subunits: the heavy chain and the light chain, connected via disulfide bonds. Each heavy chain and light chain is further divided into a variable or a constant region. The variable regions interact most directly with the antigen and further comprise three hyper variable regions (complementarity determining domains, CDRs). Thus, a single antibody comprising two heavy chains and two light chains comprises a total of 12 CDRs (three for each heavy chain and each light chain). However, each of the variable regions, particularly the CDRs, possess some degree of affinity for the antigen and maximum affinity can be achieved with a single heavy chain coupled to a single light chain. For this reason, a typical IgG antibody is considered divalent and can potentially target two different antigens simultaneously depending on the identity of the heavy and light chains.

The variable region of the antibody (both the heavy and light chains) is collectively known as the Fab fragment and can be cleaved from the constant region (known as the Fc portion) to form an antigen-binding fragment. Antigen-binding fragments can also include inter alia, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. Regardless of structure, the antigen-binding fragment binds with the same antigen that is recognized by the intact immunoglobulin. An antigen-binding fragment can comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the binding molecule. In addition, as noted each of the CDRs possess some degree of affinity for the antigen, and can each be considered an antigen-binding fragment. An antibody fragment can have an equivalent binding affinity for the target as the parent antibody. Both divalent and monovalent antibody fragments are included in the present invention. The fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, Edited by: E. Harlow and D, Lane (1988), Cold Spring Harbor Laboratory, Cold Spring Harbor, N.Y.

Therefore, the antibody or antigen-binding fragment can comprise a heavy chain variable region (or fragment thereof). Amino acid sequences of the heavy chain variable regions of the Aβ protofibril-specific antibodies described herein are provided in Table 1 below. SEQ ID NOs: 12 and 14 have less specificity for protofibrils than SEQ ID NOs: 1, 3, 5, 7, 10, 32, and 34 but still bind to Aβ.

TABLE 1

| Antibody | Amino Acid Sequence of Heavy Chain Variable Region | SEQ ID NO. |
|---|---|---|
| 108 | KGVQCQSLEESRGGLFKPTDTLTLTCTVSGIDLSSNSMSWV RQAPGNGLEWIGFIWSGGNTDYANWAKSRSTITRNTNLNT VTLKMTSLTAADTATYFCARWHPDYKTFNIWGPGTLVTV SSGQPKAPSVFPQAPCCG | SEQ ID NO: 1 |
| 113 | KGVQCQSLEESGGGLVKPGASLTLTCAASGFSFSSGYDMC WVRQAPGKGLEWIACIGIPSGSTWYASWAKGRFTISKTSST TVTLQMTSLTAADTATYFCARRGTGNNWGLWGPGTLVTV SSGQPKAPSVFPLAPCCG | SEQ ID NO: 3 |
| 502 | KGVQCQQQLVESGGGLVKPGASLTLTCTASGFSFSSGSDM CWVRQPPGKGLEWIACIGISSGSTYYANWAKGRFTISKTSS TTVTLQMTSLTAADTATYFCARAIGPFHFNLWGPGTLVTV SSGQPKAPSVFPLAPCCG | SEQ ID NO: 5 |
| 511 and 540 | KGVQCQSLEESGGDLVKPEGSLTLTCTASGFSFSTNYDMC WVRQAPGKGLEWIACVGAGSGSTYYASWAKGRFTISKTSS TTVTLQMTSLTAADTATYFCARWTSGLYINFWGPGTLVTV SSGQPKAPSVFPLAPCCG | SEQ ID NO: 7 |
| 519 | KGVQCQQQLVESGGGLVKPGASLTLTCKASGFSFSSAYDM CWVRQAPGKGLEWIACIGCSSGTTYYATWAKGRFTISKTS STTVTLQMTSLTAADTATYFSARAQSPFHFNLWGPGTLVA VSSGQPKAPSVFPLAPCCG | SEQ ID NO: 32 |
| 531 | KGVQCQSLEESGGDLVKPEGSLTLTCTASGFSFSSNYDMC WVRQAPGKGLQWIACVGDSGHTYYASWAKGRFTISKTSS TTVTLQMTSLTAADTATYFCARWTSGLYINFWGPGTLVTV SSGQPKAPSVFPLAPCCG | SEQ ID NO: 34 |
| 545 | KGVQCQQQLVESGGGLVKPGASLTLTCKASRFSFSSAYDM GWVRQAPGKGLEWIACIGSSSGTTYYASWAKGRFTISKTS STTVTLQMTSLTAADTATYFCARAQSPFHFNLWGPGTLVA VSSGQPKAPSVFPLAPCCG | SEQ ID NO: 10 |
| 513 | KGVQCQQQLVESGGGLVKPGASLTLTCTASGFSFSRYSDM CWVRQPPGKGLEWIACIGISSGTTYYASWAKGRFTISKTSS TTVTLQMTSLTAADTATYLCTRAIGPFHFNLWGPGTLVTV SSGQPKAPSVFPLAPCCG | SEQ ID NO: 12 |

TABLE 1-continued

| Antibody | Amino Acid Sequence of Heavy Chain Variable Region | SEQ ID NO. |
|---|---|---|
| 550 | KGVQCQQQLVESGGGLVKPGASLTLTCTASGFSFSRDSDM CWVRQPPGKGLEWIACIGISSGITYYANWARGRFTISKTSS TTVTLQMTSLTAADTATYFCARAIGPFHFNLWGPGTLVTV SSGQPKAPSVFPLAPCCG | SEQ ID NO: 14 |

The heavy chain variable region of the antibody or antigen-binding fragment provided herein can comprise an amino acid sequence comprising any one of SEQ ID NOs: 1, 3, 5, 7, 10, 32, 34, 12, and 14. For example, the heavy chain variable region can comprise an amino acid sequence comprising any one of SEQ ID NOs: 1, 3, 5, 7, 10, 32, and 34. The heavy chain variable region can have an amino acid sequence consisting of or consisting essentially of any one of SEQ ID NOs: 1, 3, 5, 7, 10, 32, and 34.

The antibody or antigen-binding fragment can comprise a light chain variable region (or fragment thereof). Sequences of the light chain variable regions of Aβ protofibril-specific antibodies are provided in Table 2 below. SEQ ID NOs: 13 and 15 have less specificity for protofibrils than SEQ ID NOs: 2, 4, 6, 8, 9, 11, and 33 but still bind to Aβ.

TABLE 2

| Antibody | Amino Acid Sequence of Light Chain Variable Region | SEQ ID NO. |
|---|---|---|
| 108 | LPGATFAIVMTQTPSSKSVPVGDTVTINCQASESVYGNNRL AWFQQKPGQPPKLLIYLASNLASGVPSRFKGSGSGTQFTLT ISDVVCDDAATYYCGGYKSSTGDDLAFGGGTEVVVKGDP VAP | SEQ ID NO: 2 |
| 113 | LPGATFAIVMTQTPSSKSVPVGDTVTINCQASESVYSNNRL AWFRQKPGQPPKLLIYYASTLASGVPSRFKGSGSGTQFTLT ISDVVCDDAATYYCAGYKSASIDGDAFGGGTEVVVKGDP VAP | SEQ ID NO: 4 |
| 502 | LPGATFAIVMTQTPSSKSVPVGDTVTINCQASESVYSNNRL AWYQQKPGQPPKLLIYGASTLASGVPSRFKGSGSGTQFTLT ISDVVCDDAATYYCAGYKSGIGDGIAFGGGTEVVVKGDPV AP | SEQ ID NO: 6 |
| 511 and 540 | LPGATFAIVMTQTPSSKSVPVGDTVTINCQASESVYSNNRL AWFQQKPGQPPKLLIYLASTLASGVPSRFKGSGSGTQFTLTI SDVVCDDAATYYCTGYKSSNTDGIGFGGGTEVVVKGDPV AP | SEQ ID NO: 8 |
| 519 | LPGATFAIVMTQTPSSKSVPVGDTVTINCQASESVYSNNRL AWYQQKPGQPPKLLIYGASTLASGVPSRFKGSGSGTQFTLT ISDVVCDDAATYYCAGYKSSTTDGFAFGGGTEVVVKGDP VAP | SEQ ID NO: 33 |
| 531 | LPGATFAIVMTQTPSSKSVPVGDTVTISCQASESVYSNNRL AWFQQKPGQPPKLLIYLASTLASGVPSRFKGSGSGTQFTLTI SDVVCDDAATYYCAGYKISNTDGIGFGGGTEVVVKGDPV AP | SEQ ID NO: 9 |
| 545 | LPGATFAIVMTQTPSSKSVPVGDTVTINCQASESVYSNNRL AWYQQKPGQPPKLLIYGASTLASGVPSRFKGSGSGTQFTLT ISDVVCDDAATYYCAGYKSSSTDGFAFGGGTEVVVKGDP VAP | SEQ ID NO: 11 |
| 513 | LPGATFAIVMTQTPSSRSVPVGDTVTISCQASESVYNNNRL AWYQQKAGQPPKLLIYGASTLASGVPSRFKGSGSGTQFTL TISDVVCDDAATYYCAGYKSGSTDGCAFGGGTEVVVKGD PVAP | SEQ ID NO: 13 |
| 550 | LPGATFAIVMTQTPSSKSVPVGDTVTIDCQASESVYSKNRL AWYQQKPGQPPKLLIYGASTLASGVPSRFKGSGSGTQFTLT VSDVVCDDAATYYCAGYKSGIGDGIAFGGGTEVVVKGDP VAP | SEQ ID NO: 15 |

The light chain variable region can comprise an amino acid sequence comprising any one of SEQ ID NOs: 2, 4, 6, 8, 9, 11, 33, 13, and 15. For example, the light chain variable region can comprise an amino acid sequence comprising any one of SEQ ID NOs: 2, 4, 6, 8, 9, 11, and 33. The light chain variable region can comprise an amino acid sequence consisting or consisting essentially of any one of SEQ ID NOs: 2, 4, 6, 8, 9, 11, and 33.

Hypervariable and Framework Regions

As is understood in the art, each of the heavy and light chain variable regions comprise three complementary defining regions (CDRs) classified as $CDR_{H1}$, $CDR_{H2}$, and $CDR_{H3}$ (for the heavy chain) and as $CDR_{L1}$, $CDR_{L2}$, and $CDR_{L3}$ (for the light chain). The term "complementarity determining regions" (CDR) as used herein means sequences within the variable regions of antibodies that usually contribute to a large extent to the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of posttranslational modifications of proteins.

CDR regions are known to be highly specific for antigen binding and are framed by more conserved Framework (FR) regions. It is readily apparent to one of ordinary skill that combining various framework and complementary regions taken from the heavy and light chains provided herein can generate more antibodies having the same properties and binding affinity of the antibodies described here. However, the resulting heavy and light chain variable regions will not comprise a sequence having 100% identity to the sequences provided above. Therefore, one of ordinary skill can immediately appreciate that various antibodies comprising amino acid sequences having a certain percent identity (% identity) to the sequences provided above may also be included in the present invention.

Therefore, since many conservative substitutions may be envisioned by one of ordinary skill in the art without affecting the activity of the antibody, the antibody or antibody binding fragment can comprise a heavy chain variable region comprising at least 70% sequence identity to any one of SEQ ID NOs 1, 3, 5, 7, 10, 32, 34, 12, and 14.

For example, the antibody or antigen-binding fragment thereof can comprise a heavy chain variable region having at least 75% sequence identity to any one of SEQ ID NOs: 1, 3, 5, 7, 10, 32, 34, 12, and 14.

The antibody or antigen-binding fragment thereof can comprise a heavy chain variable region having at least 80% sequence identity to any one of SEQ ID NOs: 1, 3, 5, 7, 10, 32, 34, 12, and 14.

The antibody or antigen-binding fragment thereof can comprise a heavy chain variable region having at least 85% sequence identity to any one of SEQ ID NOs: 1, 3, 5, 7, 10, 32, 34, 12, and 14.

The antibody or antigen-binding fragment thereof can comprise a heavy chain variable region having at least 90% sequence identity to any one of SEQ ID NOs: 1, 3, 5, 7, 10, 32, 34, 12, and 14.

The antibody or antigen-binding fragment thereof can comprise a heavy chain variable region having at least 95% sequence identity to any one of SEQ ID NOs: 1, 3, 5, 7, 10, 32, 34, 12, and 14.

The antibody or antigen-binding fragment thereof can comprise a heavy chain variable region having at least 96% sequence identity to any one of SEQ ID NOs: 1, 3, 5, 7, 10, 32, 34, 12, and 14.

The antibody or antigen-binding fragment thereof can comprise a heavy chain variable region having at least 97% sequence identity to any one of SEQ ID NOs: 1, 3, 5, 7, 10, 32, 34, 12, and 14.

The antibody or antigen-binding fragment thereof can comprise a heavy chain variable region having at least 98% sequence identity to any one of SEQ ID NOs: 1, 3, 5, 7, 10, 32, 34, 12, and 14.

The antibody or antigen-binding fragment thereof can comprise a heavy chain variable region having at least 99% sequence identity to any one of SEQ ID NOs: 1, 3, 5, 7, 10, 32, 34, 12, and 14.

Likewise, since many conservative substitutions may be envisioned by one of ordinary skill in the art without affecting the activity of the antibody, the antibody or antibody binding fragment can comprise a light chain variable region comprising at least 70% sequence identity to any one of SEQ ID NOs: 2, 4, 6, 8, 9, 11, 33, 13, and 15.

The light chain variable region of the antibody or antigen-binding fragment thereof can comprise at least 75% sequence identity to any one of SEQ ID NOs: 2, 4, 6, 8, 9, 11, 33, 13, and 15.

The light chain variable region of the antibody or antigen-binding fragment thereof can comprise at least 80% sequence identity to any one of SEQ ID NOs: 2, 4, 6, 8, 9, 11, 33, 13, and 15.

The light chain variable region of the antibody or antigen-binding fragment thereof can comprise at least 85% sequence identity to any one of SEQ ID NOs: 2, 4, 6, 8, 9, 11, 33, 13, and 15.

The light chain variable region of the antibody or antigen-binding fragment thereof can comprise at least 90% sequence identity to any one of SEQ ID NOs: 2, 4, 6, 8, 9, 11, 33, 13, and 15.

The light chain variable region of the antibody or antigen-binding fragment thereof can comprise at least 95% sequence identity to any one of SEQ ID NOs: 2, 4, 6, 8, 9, 11, 33, 13, and 15.

The light chain variable region of the antibody or antigen-binding fragment thereof can comprise at least 96% sequence identity to any one of SEQ ID NOs: 2, 4, 6, 8, 9, 11, 33, 13, and 15.

The light chain variable region of the antibody or antigen-binding fragment thereof can comprise at least 97% sequence identity to any one of SEQ ID NOs: 2, 4, 6, 8, 9, 11, 33, 13 and 15.

The light chain variable region of the antibody or antigen-binding fragment thereof can comprise at least 98% sequence identity to any one of SEQ ID NOs: 2, 4, 6, 8, 9, 11, 33, 13, and 15.

The light chain variable region of the antibody or antigen-binding fragment thereof can comprise at least 99% sequence identity to any one of SEQ ID NOs: 2, 4, 6, 8, 9, 11, 33, 13, and 15.

Amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Further, the heavy and light chains provided (including heavy and light chains having at least 70% sequence identity to those provided above) may be combined in various ways to form new antibodies. Illustrative combinations of the heavy and light variable regions are described below.

The antibody or antigen-binding fragment can comprise an immunoglobulin heavy chain variable region having an amino acid sequence comprising SEQ ID NO: 1.

The antibody or antigen-binding fragment can comprise an immunoglobulin heavy chain variable region having an amino acid sequence comprising SEQ ID NO: 3.

The antibody or antigen-binding fragment can comprise an immunoglobulin heavy chain variable region having an amino acid sequence comprising SEQ ID NO: 5.

The antibody or antigen-binding fragment can comprise an immunoglobulin heavy chain variable region having an amino acid sequence comprising SEQ ID NO: 7.

The antibody or antigen-binding fragment can comprise an immunoglobulin heavy chain variable region having an amino acid sequence comprising SEQ ID NO: 10.

The antibody or antigen-binding fragment can comprise an immunoglobulin heavy chain variable region having an amino acid sequence comprising SEQ ID NO: 32.

The antibody or antigen-binding fragment can comprise an immunoglobulin heavy chain variable region having an amino acid sequence comprising SEQ ID NO: 34.

The antibody or antigen-binding fragment can comprise an immunoglobulin heavy chain variable region having an amino acid sequence comprising SEQ ID NO: 12.

The antibody or antigen-binding fragment can comprise an immunoglobulin heavy chain variable region having an amino acid sequence comprising SEQ ID NO: 14.

The antibody or antigen-binding fragment can comprise an immunoglobulin light chain variable region having an amino acid sequence comprising SEQ ID NO: 2.

The antibody or antigen-binding fragment can comprise an immunoglobulin light chain variable region having an amino acid sequence comprising SEQ ID NO: 4.

The antibody or antigen-binding fragment can comprise an immunoglobulin light chain variable region having an amino acid sequence comprising SEQ ID NO: 6.

The antibody or antigen-binding fragment can comprise an immunoglobulin light chain variable region having an amino acid sequence comprising SEQ ID NO: 8.

The antibody or antigen-binding fragment can comprise an immunoglobulin light chain variable region having an amino acid sequence comprising SEQ ID NO: 9.

The antibody or antigen-binding fragment can comprise an immunoglobulin light chain variable region having an amino acid sequence comprising SEQ ID NO: 11.

The antibody or antigen-binding fragment can comprise an immunoglobulin light chain variable region having an amino acid sequence comprising SEQ ID NO: 33.

The antibody or antigen-binding fragment can comprise an immunoglobulin light chain variable region having an amino acid sequence comprising SEQ ID NO: 13.

The antibody or antigen-binding fragment can comprise an immunoglobulin light chain variable region having an amino acid sequence comprising SEQ ID NO: 15.

The antibody or antigen-binding fragment can comprise an immunoglobulin heavy chain variable region having an amino acid sequence comprising SEQ ID NO: 1 and an immunoglobulin light chain variable region having an amino acid sequence comprising SEQ ID NO: 2.

The antibody or antigen-binding fragment can comprise an immunoglobulin heavy chain variable region having an amino acid sequence comprising SEQ ID NO: 3 and an immunoglobulin light chain variable region having an amino acid sequence comprising SEQ ID NO: 4.

The antibody or antigen-binding fragment can comprise an immunoglobulin heavy chain variable region having an amino acid sequence comprising SEQ ID NO: 5 and an immunoglobulin light chain variable region having an amino acid sequence comprising SEQ ID NO: 6.

The antibody or antigen-binding fragment can comprise an immunoglobulin heavy chain variable region having an amino acid sequence comprising SEQ ID NO: 7 and an immunoglobulin light chain variable region having an amino acid sequence comprising SEQ ID NO: 8.

The antibody or antigen-binding fragment can comprise an immunoglobulin heavy chain variable region having an amino acid sequence comprising SEQ ID NO: 10 and an immunoglobulin light chain variable region having an amino acid sequence comprising SEQ ID NO: 11.

The antibody or antigen-binding fragment can comprise an immunoglobulin heavy chain variable region having an amino acid sequence comprising SEQ ID NO: 32 and an immunoglobulin light chain variable region having an amino acid sequence comprising SEQ ID NO: 33.

The antibody or antigen-binding fragment can comprise an immunoglobulin heavy chain variable region having an amino acid sequence comprising SEQ ID NO: 34 and an immunoglobulin light chain variable region having an amino acid sequence comprising SEQ ID NO: 9.

The antibody or antigen-binding fragment can comprise an immunoglobulin heavy chain variable region having an amino acid sequence comprising SEQ ID NO: 12 and an immunoglobulin light chain variable region having an amino acid sequence comprising SEQ ID NO: 13.

The antibody or antigen-binding fragment can comprise an immunoglobulin heavy chain variable region having an amino acid sequence comprising SEQ ID NO: 14 and an immunoglobulin light chain variable region having an amino acid sequence comprising SEQ ID NO: 15.

Derivatives and Synthetically Synthesized Antibodies or Binding Moieties

Also provided are peptides, polypeptides and/or proteins derived from any of the antibodies or antibody binding fragments described herein, including an intact antibody or antigen-binding fragment that has been modified, engineered or chemically conjugated. Generally, as used herein, the derivatives provided here are substantially similar to the antibodies or antibody binding fragments described herein. For example, they may contain one or more conservative substitutions in their amino acid sequences or may contain a chemical modification. The derivatives and modified peptides/polypeptides/proteins are all considered "structurally similar" which means they retain the overall secondary, tertiary and/or quaternary structure of the parent molecule and are expected to interact with to the antigen in the same way as the parent molecule (e.g., have a similar binding affinity).

A class of synthetically derived antibodies or antigen-binding moieties can be generated by conservatively mutating residues on the parent molecule to generate a peptide, polypeptide or protein maintaining the same activity as the parent molecule. Representative conservative substitutions are known in the art and are also summarized here.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine).

Deletion is the replacement of an amino acid by a direct bond. Positions for deletions include the termini of a polypeptide and linkages between individual protein domains. Insertions are introductions of amino acids into the polypeptide chain, a direct bond being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in vitro using the specific codon-usage of the desired host cell.

A second way to generate a functional peptide/polypeptide or protein based on the sequences provided herein is through the use of computational, "in-silico" design. For example, computationally designed antibodies or antigen-binding fragments may be designed using standard methods of the art. For example, see Strauch E M et al., (Nat Biotechnol. 2017 July; 35(7):667-671), Fleishman S J et al., (Science. 2011 May 13; 332(6031):816-21), and Koday M T et al., (PLoS Pathog. 2016 Feb. 4; 12(2):e1005409), each incorporated by reference in their entirety.

Binding and Function of the Antibodies and Antigen-Binding Fragments

The antibodies and antigen-binding fragments thereof described herein all have some measure of binding affinity to Aβ. Preferably, the antibodies and antigen-binding fragments thereof have selective binding affinity to Aβ protofibrils. For example, the antibodies or antigen-binding fragments thereof bind to Aβ protofibrils with a binding affinity of about 1 nM to about 10 nM. As used herein, "binding affinity" refers to the equilibrium dissociation constant ($K_D$) of the antibody which may be determined according to any standard methods in the art. For example, see Ma et al., (*J Pharm Anal.* 2018 May 5; 8(3):147-152) incorporated herein by reference in its entirety.

Preferably, the antibodies and antigen-binding fragments thereof have little or no cross-reactivity to Aβ monomers or insoluble fibers. Illustrative antibodies and antigen-binding fragments having this conformational selectivity for Aβ protofibrils include those having a heavy chain variable region comprising, consisting essentially of, or consisting of any one of SEQ ID NOs: 1, 3, 5, 7 10, 32, and 34 and/or having a light chain variable region comprising, consisting essentially of, or consisting of any one of SEQ ID NOs: 2, 4, 6, 8, 9, 11, and 33.

Preferably, the antibodies and antigen-binding fragments thereof inhibit aggregation of Aβ42 monomers at substoichiometric ratios of antibody or antigen-binding fragment to Aβ42 monomers. For example, the antibodies and antigen-binding fragments thereof preferably inhibit aggregation of Aβ42 monomers at a molar ratio of about 0.005 to about 1 of antibody or antigen-binding fragment to Aβ42 monomer. Even more preferably, the antibodies and antigen-binding fragments thereof inhibit aggregation of Aβ42 monomers at a molar ratio of about 0.01 to about 0.1 of antibody or antigen-binding fragment to Aβ42 monomer.

The antibodies and antigen-binding fragments may preferentially bind to the N-terminal region of the protofibrils.

The term "specifically binds" or "selectively binds" are used interchangeably herein in reference to the interaction of an antibody and its binding partner, e.g. an antigen. These terms mean that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the terms "specifically binds" and "selectively binds" mean immunospecifically binding to an antigenic determinant or epitope and not immunospecifically binding to other antigenic determinants or epitopes. An antibody that immunospecifically binds to an antigen may bind to other peptides or polypeptides with lower affinity as determined by, e.g., radioimmunoassays (MA), enzyme-linked immunosorbent assays (ELISA), BIACORE, or other assays known in the art. Antibodies or fragments thereof that immunospecifically bind to an antigen may be cross-reactive with related antigens carrying the same epitope. Preferably, antibodies or fragments thereof that immunospecifically bind to an antigen do not cross-react with other antigens.

Humanized, Monoclonal and IgG antibodies

The antibody or antigen-binding fragment can be humanized. "Humanized" antibodies are generally chimeric or mutant monoclonal antibodies from mouse, rat, hamster, rabbit or other species, bearing human constant and/or variable region domains or specific changes. Techniques for generating a so-called "humanized" antibody are well known to those of skill in the art.

The antibody or antigen-binding fragment can be a monoclonal antibody or antigen-binding fragment.

The antibody or antigen-binding fragment can be an IgG type antibody or antigen-binding fragment.

Antibody Production

Methods for producing antibodies are known in the art. For example, DNA molecules encoding light chain variable regions and/or heavy chain variable regions can be chemically synthesized. Synthetic DNA molecules can be ligated to other appropriate nucleotide sequences, including, e.g., constant region coding sequences, and expression control sequences, to produce conventional gene expression constructs encoding the desired antibody. Production of defined gene constructs is within routine skill in the art.

Nucleic acids encoding desired antibodies can be incorporated (ligated) into expression vectors, which can be introduced into host cells through conventional transfection or transformation techniques. Illustrative host cells are *E. coli* cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon, and, optionally, may contain enhancers, and various introns. This expression vector optionally contains sequences encoding all or part of a constant region, enabling an entire, or a part of, a heavy or light chain to be expressed. The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). A host cell can be transfected with a single vector expressing a polypeptide expressing an entire, or part of, a heavy chain (e.g., a heavy chain variable region) or a light chain (e.g., a light chain variable region). Alternatively, a host cell can be transfected with a single vector encoding (a) a polypeptide comprising a heavy chain variable region and a polypeptide comprising a light chain variable region, or (b) an entire immunoglobulin heavy chain and an entire immunoglobulin light chain. As another alternative, a host cell can be co-transfected with more than one expression vector (e.g., one expression vector encoding a polypeptide comprising an entire, or part of, a heavy chain or heavy chain variable region, and another expression vector encoding a polypeptide comprising an entire, or part of, a light chain or light chain variable region).

The term "host", as used herein, is intended to refer to an organism or a cell into which a vector such as a cloning vector or an expression vector has been introduced. The organism or cell can be prokaryotic or eukaryotic. Preferably, the hosts are isolated host cells, e.g., host cells in culture. The term "host cells" merely signifies that the cells are modified to express or overexpress the antibodies of the invention and include B-cells that originally express these antibodies and which cells have been modified to over-express the binding molecule by immortalization, amplification, enhancement of expression, etc.

A polypeptide comprising an immunoglobulin heavy chain variable region or light chain variable region can be produced by growing (culturing) a host cell transfected with an expression vector encoding such variable region, under conditions that permit expression of the polypeptide. Following expression, the polypeptide can be harvested and purified or isolated using techniques known in the art, e.g., using affinity tags such as glutathione-S-transferase (GST) and histidine tags.

A monoclonal antibody that binds Aβ, preferably Aβ protofibrils, or an antigen-binding fragment of the antibody, can be produced by growing (culturing) a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment of the antibody) can be harvested and purified or isolated using techniques known in the art, e.g., Protein A, Protein G, affinity tags such as glutathione-S-transferase (GST) and histidine tags. It is within ordinary skill in the art to express the heavy chain and the light chain from a single expression vector or from two separate expression vectors.

A nucleic acid is provided, the nucleic acid comprising a nucleotide sequence encoding the antibody or antigen-binding fragment described herein. The skilled artisan will appreciate that functional variants of these nucleic acid molecules are also intended to be a part of the present invention. Functional variants are nucleic acid sequences that can be directly translated, using the standard genetic code, to provide an amino acid sequence identical to that translated from the parental nucleic acid molecules.

The nucleic acid can comprise a nucleotide sequence encoding an immunoglobulin heavy chain variable region of the antibody or antigen-binding fragment described herein. The nucleic acid can comprise a nucleotide sequence encoding an immunoglobulin light chain variable region of the antibody or antigen-binding fragment described herein. As described above, a single nucleic acid may be provided that encodes more than one protein product (e.g., the immunoglobulin light chain and the immunoglobulin heavy chain). Alternatively, two or more separate nucleic acids may be provided each encoding one component of the antibody and/or antigen-binding fragment (e.g., the light chain or the heavy chain).

Illustrative nucleic acid sequences that can be used to encode the heavy and light chains of the antibodies described herein are provided in Table 3 below. Note that each sequence encodes an amino acid chain identified above in Tables 1 and 2. For ease of reference, the SEQ ID NO. that corresponds to the encoded amino acid for each nucleic acid sequence is also provided.

TABLE 3

| Name | Sequence | Nucleic Acid SEQ ID NO: | Amino Acid SEQ ID NO: |
|------|----------|-------------------------|-----------------------|
| 108-Heavy | AAAGGTGTCCAGTGTCAGTCGCTGGAGGAGT CCAGGGGAGGTCTCTTCAAGCCAACGGATAC CCTGACACTCACCTGCACAGTCTCTGGAATC GACCTCAGTAGTAATTCAATGAGCTGGGTCC GCCAGGCTCCAGGGAACGGCCTGGAGTGGAT CGGATTCATTTGGAGTGGTGGTAACACAGAC TATGCGAACTGGGCGAAAAGCCGATCCACCA TCACCAGAAACACCAACCTGAACACGGTGAC TCTGAAAATGACCAGTCTGACAGCCGCGGAC ACGGCCACCTATTTCTGTGCGAGATGGCATC CTGATTATAAAACTTTTAACATCTGGGGCCC AGGCACCCTGGTCACCGTCTCCTCAGGGCAA CCTAAGGCTCCATCAGTCTTCCCACAGGCCC CCTGCTGCGGGG | SEQ ID NO: 16 | SEQ ID NO: 1 |
| 108-Light | GCTCCCAGGTGCCACATTTGCCATCGTGATG ACCCAGACTCCATCTTCCAAGTCTGTCCCTGT GGGAGACACAGTCACCATCAATTGCCAGGCC AGTGAGAGTGTTTATGGTAACAACCGCTTAG CCTGGTTTCAACAGAAACCAGGGCAGCCTCC CAAGCTCCTGATCTATCTGGCATCCAATCTGG CATCTGGGGTCCCATCGCGGTTCAAAGGCAG TGGATCTGGGACACAGTTCACTCTCACCATC AGCGATGTGGTGTGTGACGATGCTGCCACTT ACTACTGTGGAGGATATAAAAGTAGTACTGG TGATGATTTAGCTTTCGGCGGAGGGACCGAG GTGGTGGTCAAAGGTGATCCAGTTGCACCT | SEQ ID NO: 17 | SEQ ID NO: 2 |
| 113-Heavy | AAAGGTGTCCAGTGTCAGTCGTTGGAGGAGT CCGGGGGAGGCCTGGTCAAGCCTGGGGCATC CCTGACACTCACCTGCGCAGCCTCTGGATTCT CCTTCAGTAGCGGCTACGACATGTGCTGGGT CCGCCAGGCTCCAGGGAAGGGGCTGGAGTG GATCGCATGCATTGGTATTCCTAGTGGTAGC ACATGGTACGCGAGCTGGGCGAAAGGCCGAT TCACCATCTCCAAAACCTCGTCGACCACGGT GACTCTGCAAATGACCAGTCTGACAGCCGCG GACACGGCCACCTATTTCTGTGCGAGACGTG GTACTGGTAATAATTGGGGCTTGTGGGGCCC AGGCACCCTGGTCACGGTCTCCTCAGGGCAA CCTAAGGCTCCATCAGTCTTCCCACTGGCCCC CTGCTGCGGGG | SEQ ID NO: 18 | SEQ ID NO: 3 |
| 113-Light | GCTCCCAGGTGCCACATTTGCCATCGTGATG ACCCAGACTCCATCTTCCAAGTCTGTCCCTGT GGGAGACACAGTCACCATCAATTGCCAGGCC AGTGAGAGTGTTTATAGTAACAACCGCTTAG CCTGGTTTCGACAGAAACCAGGGCAGCCTCC CAAGCTCCTGATCTATTATGCATCCACTCTGG CATCTGGGGTCCCTTCGCGGTTCAAAGGCAG TGGATCTGGGACACAGTTCACTCTCACCATC AGTGATGTGGTGTGTGACGATGCTGCCACTT ACTACTGTGCAGGATATAAAAGTGCTAGCAT TGATGGTGATGCTTTCGGCGGAGGGACCGAG GTGGTGGTCAAAGGTGATCCAGTTGCACCT | SEQ ID NO: 19 | SEQ ID NO: 4 |
| 502-Heavy | AAAGGTGTCCAGTGTCAGCAGCAGCTGGTGG AGTCCGGGGGAGGCCTGGTCAAGCCTGGGGC ATCCCTGACACTCACCTGCACAGCCTCTGGA TTCTCCTTCAGTAGCGGCAGCGACATGTGCT GGGTCCGCCAGCCTCCAGGGAAGGGGCTGGA GTGGATCGCATGCATTGGCATTAGTAGTGGT AGCACTTACTACGCGAACTGGGCGAAAGGCC GATTCACCATCTCCAAAACCTCGTCGACCAC GGTGACTCTGCAAATGACCAGTCTGACAGCC GCGGACACGGCCACCTATTTCTGTGCGAGAG CTATAGGGCCTTTCCACTTTAACTTGTGGGGC CCAGGCACCCTGGTCACCGTCTCCTCAGGGC AACCTAAGGCTCCATCAGTCTTCCCACTGGC CCCCTGCTGCGGGG | SEQ ID NO: 20 | SEQ ID NO: 5 |
| 502-Light | GCTCCCAGGTGCCACATTTGCCATCGTGATG ACCCAGACTCCATCTTCCAAGTCTGTCCCTGT GGGAGACACAGTCACCATCAATTGCCAGGCC AGTGAGAGTGTTTATAGTAACAACCGCTTAG CCTGGTATCAGCAGAAACCAGGGCAGCCTCC CAAGCTCCTGATCTATGGTGCATCCACTCTGG | SEQ ID NO: 21 | SEQ ID NO: 6 |

TABLE 3-continued

| Name | Sequence | Nucleic Acid SEQ ID NO: | Amino Acid SEQ ID NO: |
|------|----------|-------------------------|------------------------|
| | CATCTGGGGTCCCATCGCGGTTCAAAGGCAG CGGATCTGGGACACAGTTCACTCTCACCATC AGCGATGTGGTGTGTGACGATGCTGCCACTT ACTACTGTGCAGGATATAAAAGTGGTATTGG TGATGGTATTGCTTTCGGCGGAGGGACCGAG GTGGTGGTCAAAGGTGATCCAGTTGCACCT | | |
| 511/540-<br>Heavy | AAAGGTGTCCAGTGTCAGTCGTTGGAGGAGT CCGGGGGAGACCTGGTCAAGCCTGAGGGATC CCTGACACTCACCTGCACAGCTTCTGGATTCT CCTTCAGTACCAACTACGACATGTGCTGGGT CCGCCAGGCTCCAGGGAAGGGGCTGGAGTG GATCGCATGCGTTGGTGCTGGTAGTGGTAGC ACTTACTACGCGAGCTGGGCGAAAGGCCGGT TCACCATCTCCAAAACCTCGTCGACCACGGT GACTCTGCAAATGACCAGTCTGACAGCCGCG GACACGGCCACCTATTTCTGTGCGAGATGGA CTAGTGGTCTTTATATTAACTTCTGGGGCCCA GGCACCCTGGTCACCGTCTCCTCAGGGCAAC CTAAGGCTCCATCAGTCTTCCCACTGGCCCCC TGCTGCGGGG | SEQ ID NO: 22 | SEQ ID NO: 7 |
| 511/540-<br>Light | GCTCCCAGGTGCCACATTTGCCATCGTGATG ACCCAGACTCCATCTTCCAAGTCTGTCCCTGT GGGAGACACAGTCACCATCAATTGCCAGGCC AGTGAGAGTGTTTATAGTAACAACCGCTTAG CCTGGTTTCAACAGAAACCAGGGCAGCCTCC CAAGCTCCTGATCTATCTGGCATCCACTCTGG CATCTGGGGTCCCATCGCGGTTCAAAGGCAG TGGATCTGGGACACAGTTCACTCTCACCATC AGCGATGTGGTGTGTGACGATGCTGCCACTT ACTACTGTACAGGATATAAAAGTAGTAATAC TGATGGTATCGGTTTCGGCGGAGGGACCGAG GTGGTGGTCAAAGGTGATCCAGTTGCACCT | SEQ ID NO: 23 | SEQ ID NO: 8 |
| 519-<br>Heavy | AAAGGTGTCCAGTGTCAGCAGCAGCTGGTGG AGTCCGGGGGAGGCCTGGTCAAGCCTGGGGC ATCCCTGACACTCACCTGCAAAGCCTCTGGA TTCTCCTTCAGTAGCGCCTACGACATGTGCTG GGTCCGCCAGGCTCCAGGGAAGGGGCTGGA GTGGATCGCATGCATTGGTTGTAGTAGTGGT ACCACTTACTATGCGACCTGGGCGAAAGGCC GATTCACCATCTCCAAAACCTCGTCGACCAC GGTGACTCTGCAAATGACCAGTCTGACAGCC GCGGACACGGCCACGTATTTCTCTGCGAGAG CGCAGTCCCCCTTCCACTTTAACTTGTGGGGC CCAGGCACCCTGGTCGCCGTCTCCTCAGGGC AACCTAAGGCTCCATCAGTCTTCCCACTGGC CCCCTGCTGCGGGG | SEQ ID NO: 35 | SEQ ID NO: 32 |
| 519-<br>Light | GCTCCCAGGTGCCACATTTGCCATCGTGATG ACCCAGACTCCATCTTCCAAGTCTGTCCCTGT GGGAGACACAGTCACCATCAATTGCCAGGCC AGTGAGAGTGTTTATAGTAACAACCGCTTAG CCTGGTATCAGCAGAAACCAGGGCAGCCTCC CAAGCTCCTGATCTATGGTGCATCCACTCTGG CATCTGGGGTCCCATCGCGGTTCAAAGGCAG TGGATCTGGGACACAGTTCACTCTCACCATC AGCGATGTGGTGTGTGACGATGCTGCCACTT ACTACTGTGCAGGATACAAAAGTAGTACTAC TGATGGTTTTGCTTTCGGCGGAGGGACCGAG GTGGTGGTCAAAGGTGATCCAGTTGCACCT | SEQ ID NO: 36 | SEQ ID NO: 33 |
| 531-<br>Heavy | AAAGGTGTCCAGTGTCAGTCGTTGGAGGAGT CCGGGGGAGACCTGGTCAAGCCTGAGGGATC CCTGACACTCACCTGCACAGCTTCTGGATTCT CCTTCAGTAGCAACTACGACATGTGCTGGGT CCGCCAGGCTCCAGGGAAGGGGCTGCAGTGG ATCGCATGCGTTGGTGATAGTGGTCATACTT ACTACGCGAGCTGGGCGAAAGGCCGGTTCAC CATCTCCAAAACCTCGTCGACCACGGTGACT CTGCAAATGACCAGTCTGACAGCCGCGGACA CGGCCACCTATTTCTGTGCGAGATGGACTAG TGGTCTTTATATTAATTTTTGGGGCCCAGGCA CCCTGGTCACCGTCTCCTCAGGGCAACCTAA GGCTCCATCAGTCTTCCCACTGGCCCCCTGCT GCGGGG | SEQ ID NO: 37 | SEQ ID NO: 34 |

TABLE 3-continued

| Name | Sequence | Nucleic Acid SEQ ID NO: | Amino Acid SEQ ID NO: |
|------|----------|-------------------------|------------------------|
| 531-Light | GCTCCCAGGTGCCACATTTGCCATCGTGATG ACCCAGACTCCATCTTCCAAGTCTGTCCCTGT GGGAGACACAGTCACCATCAGTTGCCAGGCC AGTGAGAGTGTTTATAGTAACAACCGCTTAG CCTGGTTTCAACAGAAACCAGGGCAGCCTCC CAAGCTCCTGATCTATCTGGCATCCACTCTGG CATCTGGGGTCCCATCGCGGTTCAAAGGCAG TGGATCTGGGACACAGTTCACTCTCACCATC AGCGATGTGGTGTGTGACGATGCTGCCACTT ACTACTGTGCAGGATATAAAATTAGTAATAC TGATGGTATCGGTTTCGGCGGAGGGACCGAG GTGGTGGTCAAAGGTGATCCAGTTGCACCT | SEQ ID NO: 24 | SEQ ID NO: 9 |
| 545-Heavy | AAAGGTGTCCAGTGTCAGCAGCAGCTGGTGG AGTCCGGGGGAGGCCTGGTCAAGCCTGGGGC ATCCCTGACACTCACCTGCAAAGCCTCTAGA TTCTCCTTCAGTAGCGCCTACGACATGGGCTG GGTCCGCCAGGCTCCAGGGAAGGGGCTGGA GTGGATCGCATGCATTGGTAGTAGTAGTGGT ACCACTTACTACGCGAGCTGGGCGAAAGGCC GATTCACCATCTCCAAAACCTCGTCGACCAC GGTGACTCTGCAAATGACCAGTCTGACAGCC GCGGACACGGCCACCTATTTCTGTGCGAGAG CGCAGTCCCCCTTCCACTTTAACTTGTGGGGC CCAGGCACCCTGGTCGCCGTCTCCTCAGGGC AACCTAAGGCTCCATCAGTCTTCCCACTGGC CCCCTGCTGCGGGG | SEQ ID NO: 25 | SEQ ID NO: 10 |
| 545-Light | GCTCCCAGGTGCCACATTTGCCATCGTGATG ACCCAGACTCCATCTTCCAAGTCTGTCCCTGT GGGAGACACAGTCACCATCAATTGCCAGGCC AGTGAGAGTGTTTATAGTAACAACCGCTTAG CCTGGTATCAACAGAAACCAGGGCAGCCTCC CAAGCTCCTGATCTATGGTGCATCCACTCTGG CATCTGGGGTCCCATCGCGGTTCAAAGGCAG TGGATCTGGGACACAGTTCACTCTCACCATC AGCGATGTGGTGTGTGACGATGCTGCCACTT ACTACTGTGCAGGATATAAAAGTAGTAGTAC TGATGGTTTTGCTTTCGGCGGAGGGACCGAG GTGGTGGTCAAAGGTGATCCAGTTGCACCT | SEQ ID NO: 26 | SEQ ID NO: 11 |
| 513-Heavy | AAAGGTGTCCAGTGTCAGCAGCAGCTGGTGG AGTCCGGGGGAGGCCTGGTCAAGCCTGGGGC ATCCCTGACACTCACCTGCACAGCCTCTGGA TTCTCCTTCAGTAGATACAGCGACATGTGCTG GGTCCGCCAGCCTCCAGGGAAGGGGCTGGAG TGGATCGCATGTATTGGCATTAGTAGTGGTA CCACTTACTACGCGAGCTGGGCGAAAGGCCG ATTCACCATCTCCAAAACCTCGTCGACCACG GTGACTCTGCAAATGACCAGTCTGACAGCCG CGGACACGGCCACCTATTTGTGTACGAGAGC TATCGGGCCTTTCCACTTTAATTTGTGGGGCC CAGGCACCCTGGTCACCGTCTCCTCAGGGCA ACCTAAGGCTCCATCAGTCTTCCCACTGGCCC CCTGCTGCGGGG | SEQ ID NO: 27 | SEQ ID NO: 12 |
| 513-Light | GCTCCCAGGTGCCACATTTGCCATCGTGATG ACCCAGACTCCATCTTCCAGGTCTGTCCCTGT GGGAGACACAGTCACCATCAGTTGCCAGGCC AGTGAGAGTGTTTATAATAACAACCGCTTAG CCTGGTATCAGCAGAAAGCAGGACAGCCTCC CAAGCTCCTGATCTATGGTGCATCCACTCTGG CATCTGGGGTCCCATCGCGGTTCAAAGGCAG CGGATCTGGGACACAGTTCACTCTCACCATC AGCGATGTGGTGTGTGACGATGCTGCCACTT ACTACTGTGCAGGATATAAAAGTGGTAGTAC TGATGGTTGTGCTTTCGGCGGAGGGACCGAG GTGGTGGTCAAAGGTGATCCAGTTGCACCT | SEQ ID NO: 28 | SEQ ID NO: 13 |
| 550-Heavy | AAAGGTGTCCAGTGTCAGCAGCAGCTGGTGG AGTCCGGGGGAGGCCTGGTCAAGCCTGGGGC ATCCCTGACACTCACCTGCACAGCCTCTGGA TTCTCCTTCAGTAGGGACAGCGACATGTGCT GGGTCCGCCAGCCTCCAGGGAAGGGGCTGGA GTGGATCGCATGTATTGGCATTAGTAGTGGT ATCACTTACTACGCGAACTGGGCGAGAGGCC | SEQ ID NO: 29 | SEQ ID NO: 14 |

TABLE 3-continued

| Name | Sequence | Nucleic Acid SEQ ID NO: | Amino Acid SEQ ID NO: |
|------|----------|-------------------------|------------------------|
| | GATTCACCATCTCCAAAACCTCGTCGACCAC GGTGACTCTGCAAATGACCAGTCTGACAGCC GCGGACACGGCCACCTATTTCTGTGCGAGAG CTATAGGGCCTTTCCACTTTAACTTGTGGGGC CCAGGCACCCTGGTCACCGTCTCCTCAGGGC AACCTAAGGCTCCATCAGTCTTCCCACTGGC CCCCTGCTGCGGGG | | |
| 550-Light | GCTCCCAGGTGCCACATTTGCCATCGTGATG ACCCAGACTCCATCTTCCAAGTCTGTCCCTGT GGGAGACACAGTCACCATCGATTGCCAGGCC AGTGAGAGTGTTTATAGTAAGAACCGCTTAG CCTGGTACCAGCAGAAACCAGGGCAGCCTCC CAAGCTCCTGATCTATGGTGCATCCACTCTGG CATCTGGGGTCCCATCGCGGTTCAAAGGCAG CGGATCTGGGACACAGTTCACTCTCACCGTC AGCGATGTGGTGTGTGACGATGCTGCCACTT ACTACTGTGCAGGATATAAAAGTGGTATTGG TGATGGTATTGCTTTCGGCGGAGGGACCGAG GTGGTGGTCAAAGGTGATCCAGTTGCACCT | SEQ ID NO: 30 | SEQ ID NO: 15 |

Therefore, the nucleic acid can comprise a nucleotide sequence comprising any one of SEQ ID NOs: 16-30 and 35-37.

Further, the nucleic acid can comprise a nucleotide sequence encoding an immunoglobulin heavy chain variable region of the antibody or antigen-binding fragment described herein. For example, the nucleic acid can comprise any one of SEQ ID NOs: 16, 18, 20, 22, 25, 35, 37, 27, and 29. Preferably, the nucleic acid comprises any one of SEQ ID NOs: 16, 18, 20, 22, 25, 35, and 37.

The nucleic acid can comprise a nucleotide sequence encoding an immunoglobulin light chain variable region of the antibody or antigen-binding fragment described herein. For example, the nucleic acid can comprise any one of SEQ ID NOs: 17, 19, 21, 23, 24, 26, 36, 28, and 30. Preferably, the nucleic acid comprises any one of SEQ ID NOs: 17, 19, 21, 23, 24, 26, and 36.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. When the nucleic acid is prepared or altered synthetically, advantage can be taken of known codon preferences of the intended host where the nucleic acid is to be expressed.

The nucleic acid may comprise cDNA.

An expression vector is provided. The expression vector comprises one or more of the nucleic acids described herein.

The term "vector" denotes a nucleic acid molecule into which a second nucleic acid molecule can be inserted for introduction into a host where it will be replicated, and in some cases expressed. A vector is capable of transporting a nucleic acid molecule to which it has been linked. Cloning as well as expression vectors are contemplated by the term "vector", as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule can be introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

Vectors can be derived from plasmids such as: F, F1, RP1, Col, pBR322, TOL, Ti, etc.; cosmids; phages such as lambda, lambdoid, M13, Mu, P1, P22, Qβ, T-even, T-odd, T2, T4, T7, etc.; or plant viruses. Vectors can be used for cloning and/or expression of the antibodies or antigen-binding fragments of the invention and might even be used for gene therapy purposes. Vectors comprising one or more nucleic acid molecules according to the invention operably linked to one or more expression-regulating nucleic acid molecules are also covered by the present invention. The choice of the vector is dependent on the recombinant procedures followed and the host used. Introduction of vectors in host cells can be affected by inter alia calcium phosphate transfection, virus infection, DEAE-dextran mediated transfection, lipofectamine transfection or electroporation. Vectors may be autonomously replicating or may replicate together with the chromosome into which they have been integrated. Preferably, the vectors contain one or more selection markers. The choice of the markers may depend on the host cells of choice. They include, but are not limited to, kanamycin, neomycin, puromycin, hygromycin, zeocin, the thymidine kinase gene from Herpes simplex virus (HSV-TK), and the dihydrofolate reductase gene from mouse (dhfr). Vectors comprising one or more nucleic acid molecules encoding the heavy and light variable chains as described above operably linked to one or more nucleic acid molecules encoding proteins or peptides that can be used to isolate the human binding molecules are also covered by the invention. These proteins or peptides include, but are not limited to, glutathione-S-transferase, maltose binding protein, polyhistidine, green fluorescent protein, luciferase and beta-galactosidase.

The term "operably linked" refers to two or more nucleic acid sequence elements that are usually physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter.

The expression vector may be transfected into a host cell to induce the translation and expression of the nucleic acid into the heavy chain variable region and/or the light chain variable region. Therefore, a host cell is provided comprising any expression vector described herein. Host cells include, but are not limited to, cells of mammalian, plant, insect, fungal or bacterial origin. Bacterial cells include, but are not limited to, cells from Gram-positive bacteria or Gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and SD can be used as host cells. Besides that, the host cells can be plant cells such as, inter alia, cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or biolistic gene transfer. Additionally, a suitable expression system can be a baculovirus system.

Expression systems using mammalian cells, such as Chinese Hamster Ovary (CHO) cells, COS cells, BHK cells, NSO cells or Bowes melanoma cells are preferred in the present invention. Mammalian cells provide expressed proteins with posttranslational modifications that are most similar to natural molecules of mammalian origin. Since the present invention deals with molecules that may have to be administered to humans, a completely human expression system would be particularly preferred. Therefore, even more preferably, the host cells are human cells. Examples of suitable human cells are inter alia HeLa, 911, AT1080, A549, HEK293, HEK293T, and FreeStyle HEK293-F cells.

Further, a method is provided for producing an antibody or antigen-binding fragment that binds Aβ42 protofibrils. The method comprises growing a host cell as described herein under conditions so that the host cell expresses a polypeptide or polypeptides comprising the immunoglobulin heavy chain variable region and the immunoglobulin light chain variable region, thereby producing the antibody or antigen-binding fragment, and purifying the antibody or antigen-binding fragment.

Pharmaceutical Compositions

Also provided are pharmaceutical compositions. The pharmaceutical compositions comprise at least one antibody or antigen-binding fragment described herein and a pharmaceutically acceptable carrier.

Pharmaceutical compositions containing one or more of the antibodies or antigen-binding fragments described herein can be formulated in any conventional manner. Proper formulation is dependent in part upon the route of administration selected. Routes of administration include, but are not limited to parenteral (e.g., intravenous, intraarterial, subcutaneous, rectal, subcutaneous, intramuscular, intraorbital, intracapsular, intraspinal, intraperitoneal, or intrasternal), topical, intravesical, intrathecal, epidural, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration. For example, the composition can be administered via infusion or injection. Preferably, the composition is administered in a manner such that it reaches the cerebrospinal fluid, for example, via intraspinal, intrathecal, or epidural injection. Dosage forms suitable for parenteral administration include solutions, suspensions, dispersions, emulsions or any other dosage form that can be administered parenterally.

Pharmaceutically acceptable carriers for use in the compositions of the present invention are selected based upon a number of factors including the particular compound used, and its concentration, stability and intended bioavailability; the subject, its age, size and general condition; and the route of administration. Generally, a pharmaceutically acceptable carrier is any inert substance that is combined with an active molecule such as a drug, agent, or antibody for preparing an agreeable or convenient dosage form. As used herein, a pharmaceutically acceptable carrier is inclusive of any pharmaceutically acceptable excipients. The "pharmaceutically acceptable excipient" is an excipient that is non-toxic to recipients at the used dosages and concentrations, and is compatible with other ingredients of the formulation comprising the drug, agent or binding molecule. Pharmaceutically acceptable excipients are widely applied and known in the art Pharmaceutically acceptable excipients are identified, for example, in *The Handbook of Pharmaceutical Excipients*, (American Pharmaceutical Association, Washington, D.C., and The Pharmaceutical Society of Great Britain, London, England, 8th Revised Edition, 2017). Additional excipients can be included in the pharmaceutical compositions of the invention for a variety of purposes. These excipients can impart properties which enhance retention of the compound at the site of administration, protect the stability of the composition, control the pH, facilitate processing of the compound into pharmaceutical compositions, and so on. Other excipients include, for example, fillers or diluents, surface active, wetting or emulsifying agents, preservatives, agents for adjusting pH or buffering agents, thickeners, colorants, dyes, flow aids, bulking agents, adsorbents, binders, disintegrating agents, lubricants, and antioxidants.

Methods of Use

The anti-Aβ protofibril antibodies described herein can be used in various applications for the treatment or monitoring of a disease or condition associated with Aβ aggregation.

A method is provided for measuring the amount of Aβ protofibrils and/or aggregated Aβ in a subject. The method comprises contacting a tissue or body fluid of the subject with any antibody or antigen-binding fragment described herein. Preferably, the antibody or antigen-binding fragment thereof has selective affinity for Aβ protofibrils over Aβ monomers or insoluble fibrils, that is, it is a conformation-specific antibody. Preferably, the antibody or antigen-binding fragment thereof has selective affinity for Aβ42 protofibrils. The tissue or body fluid of the subject can comprise cerebral spinal fluid (CSF), plasma, blood, urine, or brain tissue.

Since the antibodies provided are conformation-specific, they may also be used to detect and/or quantify amyloid protofibrils present in other diseases not associated with Aβ. Therefore, a method is provided for detecting and/or quantifying protofibrils in prion associated diseases (e.g., Alzheimer's disease, Parkinson's, Type-2 diabetes, Creutzfeldt-Jacob Disease and mad cow disease).

A method is provided for reducing an amount of Aβ protofibrils in a subject. The method comprises administering to the subject a therapeutically effective amount of any antibody or antigen-binding fragment thereof described herein. Preferably, when administered as a treatment the antibodies are humanized.

A method is also provided for treating or preventing (i.e., prophylaxis) a disease associated with Aβ protein aggregation in a subject having, or being at risk of developing said disorder. The method comprises administering to the subject a therapeutically effective amount of any antibody or antigen-binding fragment thereof described herein.

Also provided are methods for treating and/or preventing diseases associated with abnormal protofibril aggregation. The method comprises administering to the subject a therapeutically effective amount of any antibody or antigen-binding fragment thereof described herein.

The abnormal protofibril aggregation can occur with islet amyloid protein peptide (IAPP, amylin, in Type-2 diabetes), prion protein (PrP, mad cow diseases), alpha-synuclein (Parkinson's). To the extent that these conditions may be mitigated by reducing or controlling levels of protofibrils in a subject, they also may be treated or prevented by the conformation-specific antibodies described herein.

In any of the methods herein, when the antibody or antigen-binding fragment thereof is administered to a subject, it may be administered as part of a pharmaceutically acceptable composition, for example, any of the compositions described hereinabove.

When introducing elements of the present invention or the preferred embodiments(s) thereof, the articles "a", "an", "the", and "said" are intended to mean that there are one or more of the elements.

The term "and/or" means any one of the items, any combination of the items, or all of the items with which this term is associated.

The terms "comprising", "including", and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following non-limiting examples are provided to further illustrate the present invention.

Example 1: Protofibril Generation and Characterization

Preparation of Aβ peptides. Aβ42 peptides were obtained from the ERI Amyloid Laboratory, LLC (Oxford, CT) in lyophilized form and stored at −20° C. Aβ peptide was dissolved in 100% hexafluoroisopropanol (HFIP) (Sigma-Aldrich, St. Louis) to yield a 1 mM Aβ solution, separated into aliquots in sterile microcentrifuge tubes, and evaporated uncovered at room temperature overnight in a fume hood. The following day the aliquots were vacuum-centrifuged to remove any residual HFIP and stored in desiccant at −20° C. Aβ42 protofibrils were prepared as previously described (Paranj ape et al. 2012) by dissolving lyophilized Aβ (2 mg) in 50 mM NaOH to yield a 2.5 mM Aβ solution. The solution was then diluted to 250 µM Aβ in pre-filtered (0.22 µm) artificial cerebrospinal fluid (aCSF, 15 mM NaHCO₃, 1 mM Na₂HPO₄, 130 mM NaCl, 3 mM KCl, pH=7.8) incubated for 15 minutes and centrifuged at 18,000 g for 10 minutes with a Beckman-Coulter Micro-centrifuge prior to chromatographic analysis of the supernatant.

Protofibril preparations also yielded almost 50% Aβ42 monomers for further use. Alternatively, aliquots of Aβ42 were reconstituted in 6M guanidine hydrochloride (GuHCl)/ 10 mM NH₄OH to discourage protofibril formation and increase the yield of monomers. Aβ42 fibrils were prepared from purified Aβ42 monomers by incubation in low retention (siliconized) tubes for 360 h at 4° C. Fibril formation was confirmed with thioflavin T fluorescence and sedimentation by centrifugation at 18,000 g.

Size Exclusion Chromatography. Supernatants of Aβ preparation were fractionated on a SUPERDEX 75 HR 10/30 column (GE Healthcare) using an AKTA FPLC system (GE Healthcare). Prior to chromatographic isolation of Aβ, bovine serum albumin (BSA, 5 mg) taken from a sterile 7.5% fraction V solution (Sigma) was passed over the column to limit non-specific binding of Aβ to the column matrix. Following sample loading, Aβ was eluted at 0.5 mL min⁻¹ in aCSF and 0.5 mL fractions were collected and immediately placed on ice. Aβ42 and Aβ40 concentrations were determined by in-line UV absorbance using an extinction coefficient of 1450 cm⁻¹M⁻¹ at 280 nm.

Circular Dichroism. Samples (0.2 mL) were placed into a rectangular quartz cuvette with a 0.1 cm path length. Spectra were obtained by wavelength scan from 260 to 190 nm using a Jasco J-1500 circular dichroism spectrometer. Twenty successive wavelength scans were averaged for each Aβ sample. Buffer control spectra were averaged and subtracted from the Aβ sample spectra. At each resulting wavelength point, [θ]obs (degrees) was converted to mean residue ellipticity ([θ], degrees square centimeter per decimole) with the equation [θ]=[θ]obs(MRW/10lc), where MRW is the mean residue molecular weight of Aβ(1-42) (4514.1 g/mol divided by 42 residues), 1 is the optical path length (centimeters), and c is the concentration (grams per cubic centimeter).

Figure 3:
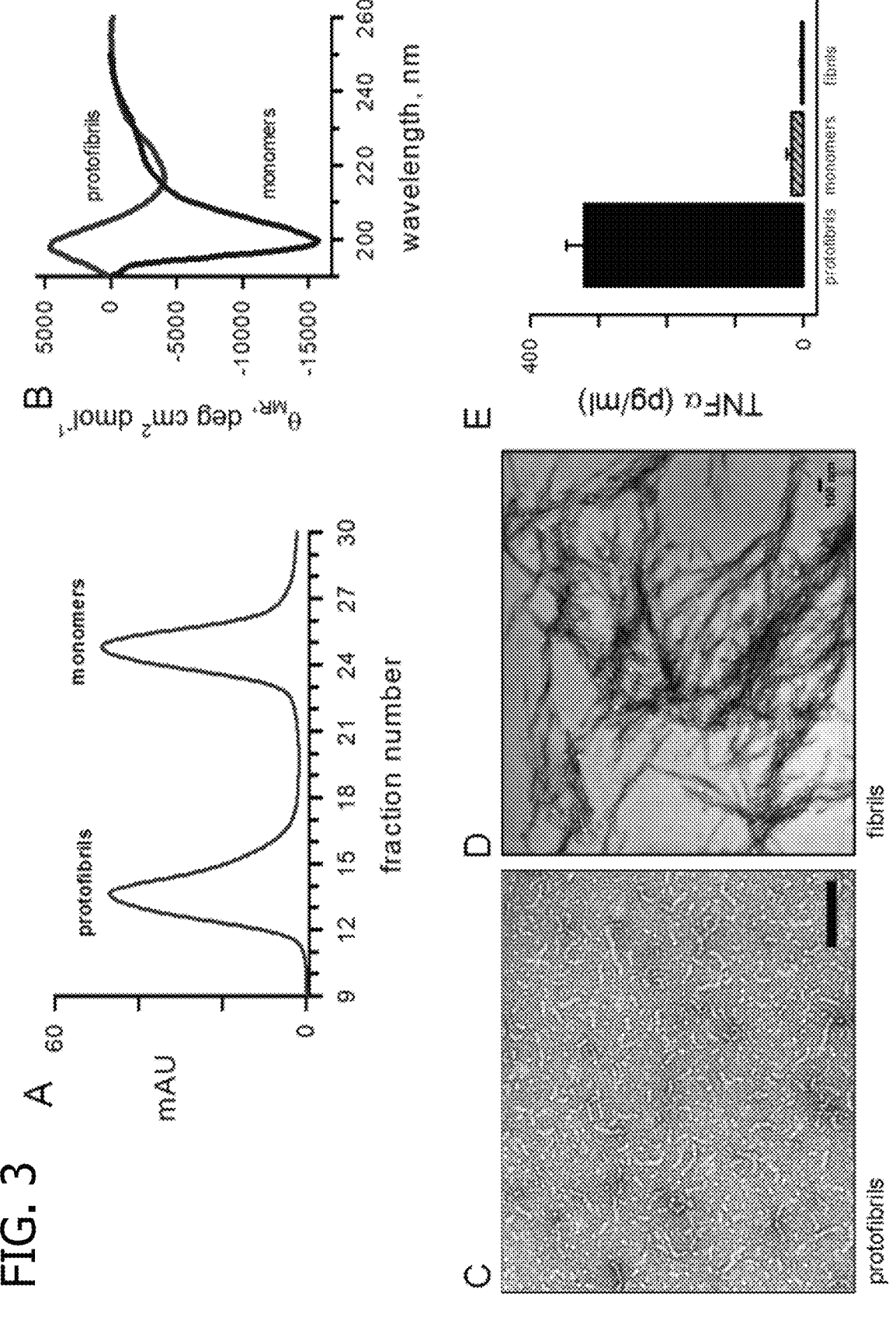
FIG. 3 shows the isolation and characterization of Aβ42 protofibrils used herein. Panel A is a size-exclusion chromatography (SEC) separation of Aβ42 protofibrils and monomers. Panel B provides a circular dichroism (CD) spectra showing β-sheet secondary structure for protofibrils and random coil for monomers. Panels C and D are representative TEM images of protofibrils (Panel C) and fibrils (Panel D) at a magnification of 43,000× (scale bar is 100 nm). Panel E is a plot showing the amount of TNFα in the culture media of microglia treated with Aβ42 protofibrils, monomers, or fibrils.

The prepared Aβ42 protofibrils were analyzed as shown in FIG. 3. Aβ42 protofibrils and monomers were separated using size exclusion chromatography (FIG. 3 panel A) and their secondary structure assessed using circular dichroism (CD) (FIG. 3, panel B). The circular dichroism analysis shows that protofibrils largely have a β-sheet conformation while monomers have a random coil structure. Protofibrils from the peak SEC fractions were pooled and analyzed by transmission electron microscopy (TEM) (FIG. 3, panels C and D). Briefly, isolated protofibrils and fibrils were diluted to 20 applied to a copper formvar grid and imaged by TEM at a magnification of 43,000× (scale bar=100 nm). Short (<100 nm) curvilinear structures were observed for isolated protofibrils (FIG. 3, panel C).

To test the functional ability of Aβ protofibrils, fibrils, and monomers to stimulate microglia, aliquots of isolated Aβ42 protofibrils, monomers and fibrils were incubated with primary murine microglia for 6 h at a final concentration of 15 µM Aβ42. Secreted TNFα was measured by ELISA in the conditioned medium. FIG. 3 panel E shows data establishing that protofibrils stimulate microglia more effectively than fibrils and cause greater release of TNFα into the media.

In addition to the data shown in FIG. 3, the protofibrils were extensively analyzed and characterized according to the methods and procedures described in Colvin et al., *JNC*

(2017), 143:736-749. The entire disclosure of Colvin et al., is incorporated herein by reference.

Example 2: Polyclonal Antibody Generation

Generation of polyclonal antibodies specific for Aβ protofibrils was performed in Colvin et al., *JNC* (2017), 143: 736-749; incorporated herein by reference in its entirety. For ease of reference, some data from this publication is reproduced and described below.

Aβ protofibrils were prepared and isolated by size exclusion chromatography (SEC) as described above in Example 1 in a modified aCSF buffering system as previously detailed (Paranjape et al. 2013). Sufficient amounts (2 mL, 0.2 mg/mL) of protofibrils were obtained and characterized prior to rabbit immunization using the method described above in Example 1. Aβ42 protofibrils, which were previously determined to range in molecular weight from 200 to 2600 kD (Nichols et al. 2015), eluted in the void volume of a SUPERDEX 75 column. These SEC-purified Aβ protofibrils were shipped overnight on ice to Pacific Immunology (Ramona, CA, USA). Pre-immune serum from two New Zealand White rabbits (PAC-10079 and PAC-10080) was obtained prior to their immunization with 0.1 mg Aβ42 protofibrils in Complete Freund's Adjuvant. Three additional immunizations were administered with 0.1 mg Aβ42 protofibrils in Incomplete Freund's Adjuvant. Five separate bleeds and an exsanguination were obtained from each rabbit and shopped to University of Missouri-St. Louis.

In vitro Characterization of Aβ42 Protofibril Anti-Serum

Figure 4:
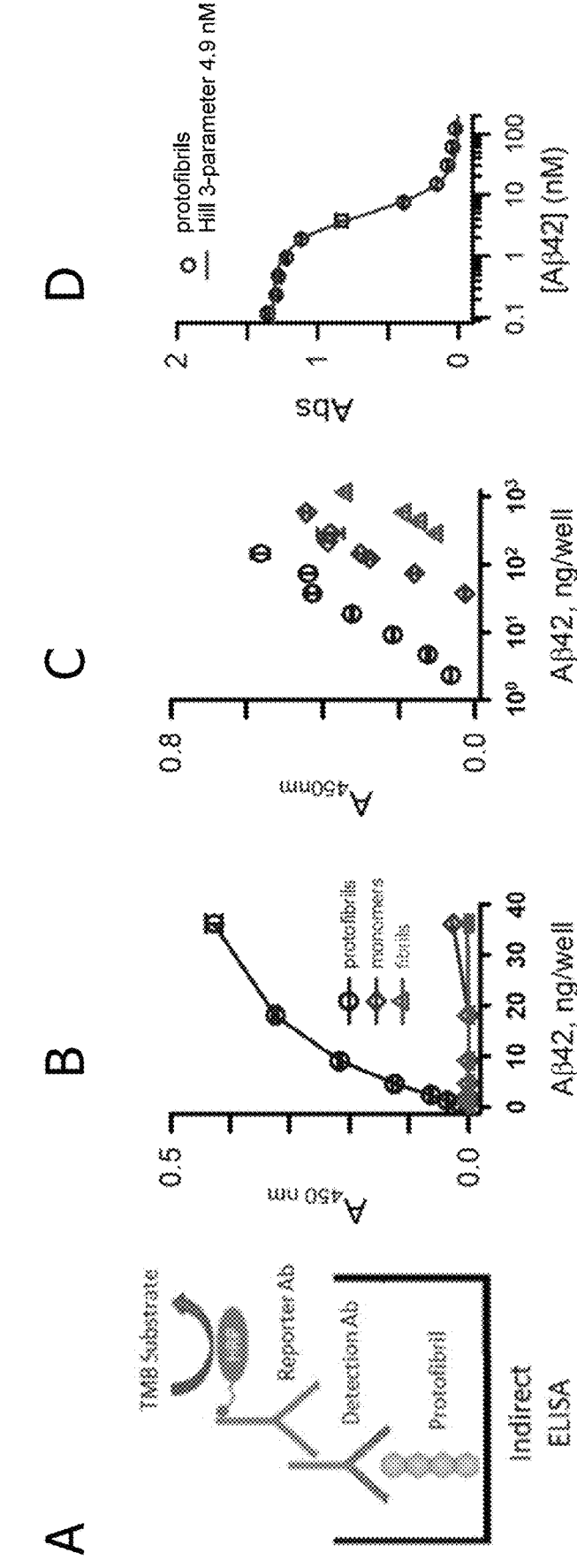
FIG. 4 depicts the results of indirect or competition ELISA assays showing selectivity of AbSL antiserum for Aβ42 protofibrils (blue, circles), relative to monomers (red, diamonds), or fibrils (green, triangles). Panel A shows a schematic of the indirect ELISA experiment used in Panels B and C indicating that absorbance is dependent on the extent of serum antibody binding to immobilized protofibrils in a well. Panel B shows indirect ELISA fluorescence relative to Aβ42 protofibril concentration per well at low levels (<40 nM/well). Panel C shows indirect ELISA absorbance relative to Aβ42 protofibril concentration per well at higher concentrations (100 to 1000 nM/well). Panel D shows the results of a competition ELISA where prior to adding the antiserum to the protofibril-coated well (as in Panel A), the AbSL antiserum is incubated with increasing concentrations of Aβ42 (indicated on the x-axis).

The pre-immune serum (PB) and all four bleeds from both rabbits were evaluated for Aβ recognition using an indirect ELISA assay as depicted in FIG. 4 panel A and described below.

Indirect ELISA. Monomeric, protofibrillar, and fibrillar Aβ (0.5 mL), prepared at various concentrations, was adsorbed overnight at 4° C. in bicarbonate buffer at pH 9.6 on a Nunc 96-well MAXISORP flat-bottom immunoplate. The wells were washed with phosphate buffered saline containing 0.05% tween (PBST) and then blocked with 150 μL PBS containing 0.01% Tween 20 and 10% milk for 1 h. All steps were done at room temperature with one PBST wash between plating and blocking steps, and four PBST washes performed between primary and secondary antibody steps. Primary antibody (AbSL anti-serum or otherwise) (0.1 mL) was added to each well for 1 h followed by 0.1 mL of secondary antibody for 2 h. An affinity-purified goat anti-rabbit (R&D Systems, Minneapolis, MN, USA HAF008, polyclonal, <5% cross-reactivity with human IgG, mouse IgG) was used. A 1:1 mixture (0.1 mL) of HRP substrate (TMB, 3,3',5,5'-tetramethylbenzidine and hydrogen peroxide) was incubated in the wells for 2 min and the reaction stopped with 0.05 mL 1 M sulfuric acid. The optical density of each sample was obtained at 450 nm with a reference reading subtracted at 620 nm using a SPECTRAMAX 340 absorbance plate reader (Molecular Devices).

FIG. 4 panel B shows the absorbance recorded at increasing concentrations of Aβ42 (ng/well) at low concentrations of Aβ. The extended Aβ42 concentration range is shown in FIG. 4 panel C and demonstrates the orders of magnitude difference in antibody recognition of different Aβ species. A competition ELISA was also performed in which wells were coated with 18 ng/well of Aβ42 protofibrils and the primary antibody was incubated with increasing concentrations of Aβ protofibrils prior to adding the antibody to coated wells. This experiment yielded a concentration response curve as shown in FIG. 4 panel D which was fit to determine an equilibrium dissociation constant ($K_D$) of 4.9 nM.

These experiments demonstrated that Aβ42 protofibril anti-serum could be generated with high affinity and specificity for Aβ42 protofibrils.

Figure 5:
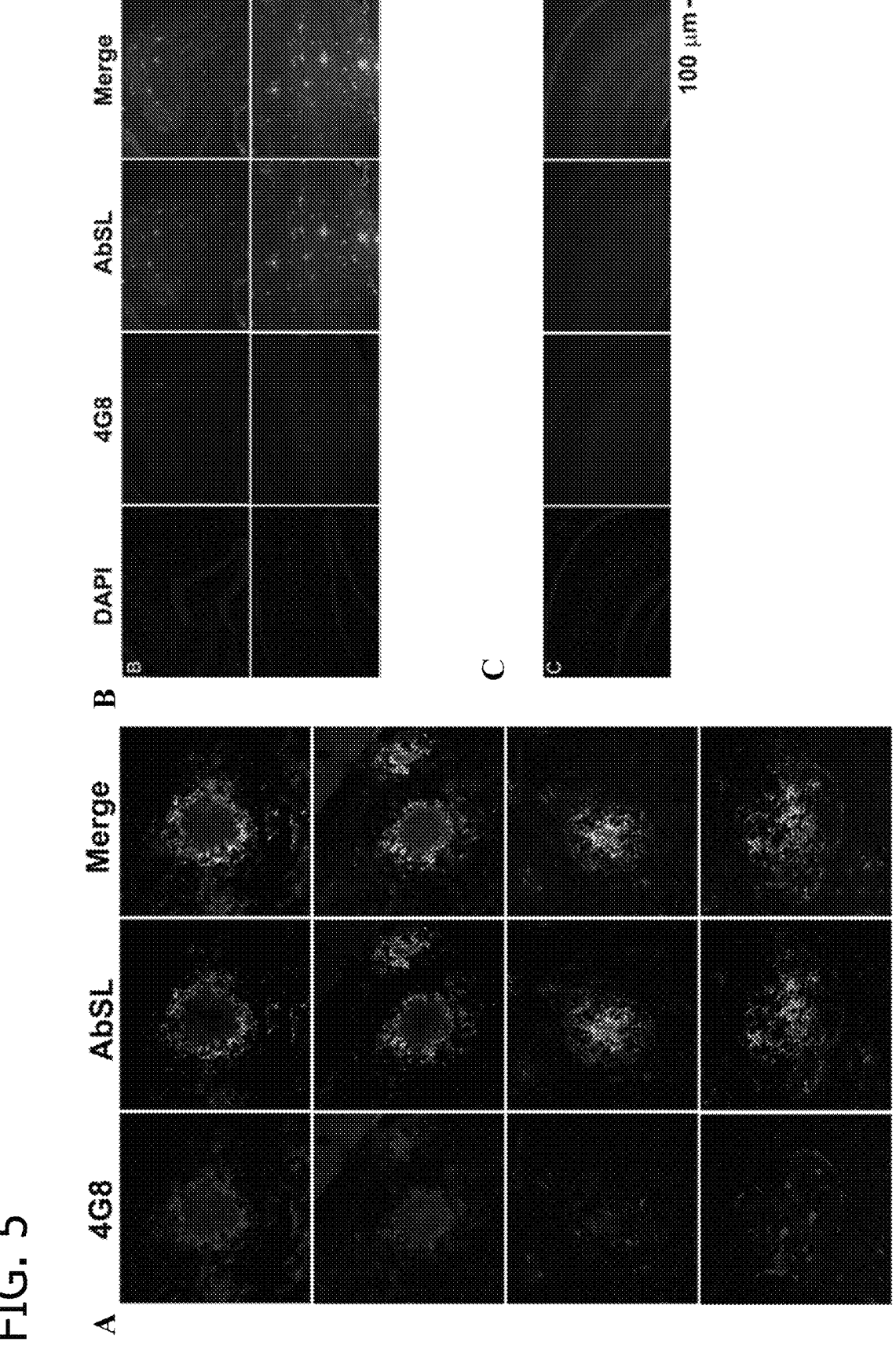
FIG. 5 shows representative confocal images of brain hemispheres (panel A) or epifluorescence images of hippocampal slices obtained from 15 month old APP/PS1 mice (panel B) or WT (panel C) mice each stained for a general anti-Aβ antibody (4G8, red) and AbSL (green) and, for panels B and C, DAPI (blue). Scale bar is 100 μm.

AbSL Antiserum Stains Distinct Pathological Amyloid Features with No Recognition of APP Brain hemispheres were prepared from 15 mo WT (C57BL/6) or amyloid precursor protein (APP)/PS1 mice, stained with 4G8 or AbSL primary antibodies, and detected with either AF594-labeled (4G8, red) or AF488-labeled (AbSL, green) secondary antibodies. 4G8 is a general A042 antibody with no conformation selectivity. Separately stained samples were imaged with either confocal (FIG. 5 panel A) or epifluorescence (FIG. 5 panels B and C) microscopy. FIG. 5 panel A shows four separate sites of amyloid accumulation in 15 mo APP/PS1 brain samples and their reactivity to 4G8 or AbSL. FIG. 5 panels B and C show hippocampal slices obtained from a 15 mo APP/PS1 (panel B) or WT (panel C) mouse and stained with DAPI (nuclei, blue), 4G8 (red) or AbSL (green).

Figure 6:
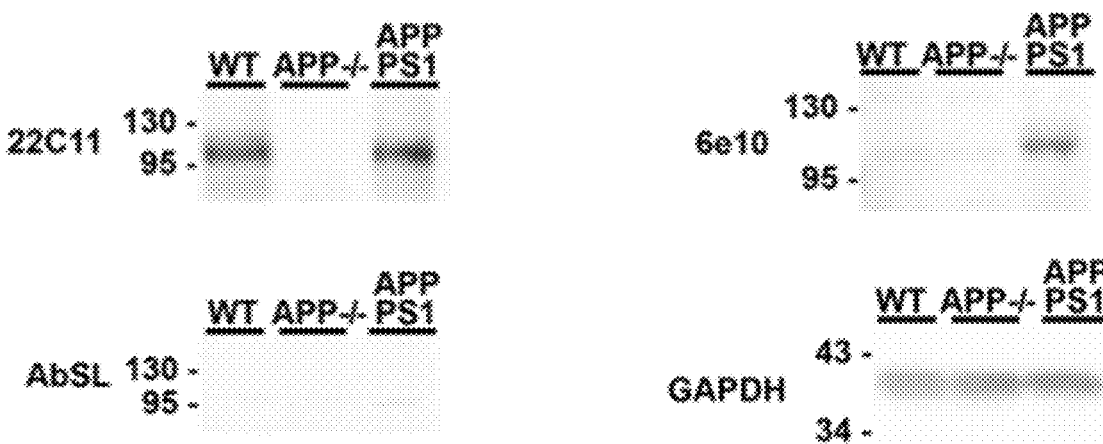
FIG. 6 shows representative western blots showing the detection of APP from WT, APP$^{-/-}$ or APP/PS1 mice using anti-APP antibodies (22C11) or anti-Aβ antibody (6e10), but not AbSL antibody. Loading controls are demonstrated with anti-GAPDH antibody.

SDS-PAGE/Western blots of mouse cortex lysates were also performed using 22C11 (APP), 6e10 (Aβ, APP), and AbSL and results are shown in FIG. 6. Briefly, temporal cortex from C57BL/6 (WT), APP$^{-/-}$, and APP/PS1 ((APPswe,PSEN1dE9)85Dbo/Mmjax) mice (Jackson Laboratory) was homogenized in radioimmunoprecipitation assay (RIPA) buffer containing protease inhibitor (Sigma Aldrich P8340) and sodium orthovanadate as a phosphatase inhibitor. The concentration of each protein homogenate was determined using the Bradford method (Bradford 1976). 10 micrograms of each protein sample was then resolved by 10% SDS-PAGE. Proteins were then transferred to PVDF membrane and blocked using a 5% BSA solution for 1 hour before application of primary antibody diluted in 5% BSA. Antibodies against full length c-terminal APP (Y188, Abcam) (22C11, Millipore), Aβ (4G8, Biolegend), human APP/Aβ (6E10, Biolegend), and GAPDH (6C5, Santa Cruz Biotechnology) as a loading control were applied at a 1:1000 dilution overnight at 4° C. AbSL anti-serum was utilized at a 1:5000 dilution in a 5% milk solution overnight at 4° C. Species specific HRP-conjugated secondary antibodies were applied to blots for two hours then blots were then washed with Tris-buffered saline containing 0.1% Tween 20 (TBS-T). Blots were visualized using chemiluminescence and images were acquired using an OMEGA Lum G imaging system. Unlike the nonspecific antibodies (22C11 and 6e10), AbSL showed no affinity for APP (bottom left corner in FIG. 6).

Affinity Purified and Biotinylated AbSL (apAbL-Biotin) Retains Protofibril Selectivity.

Figure 7:
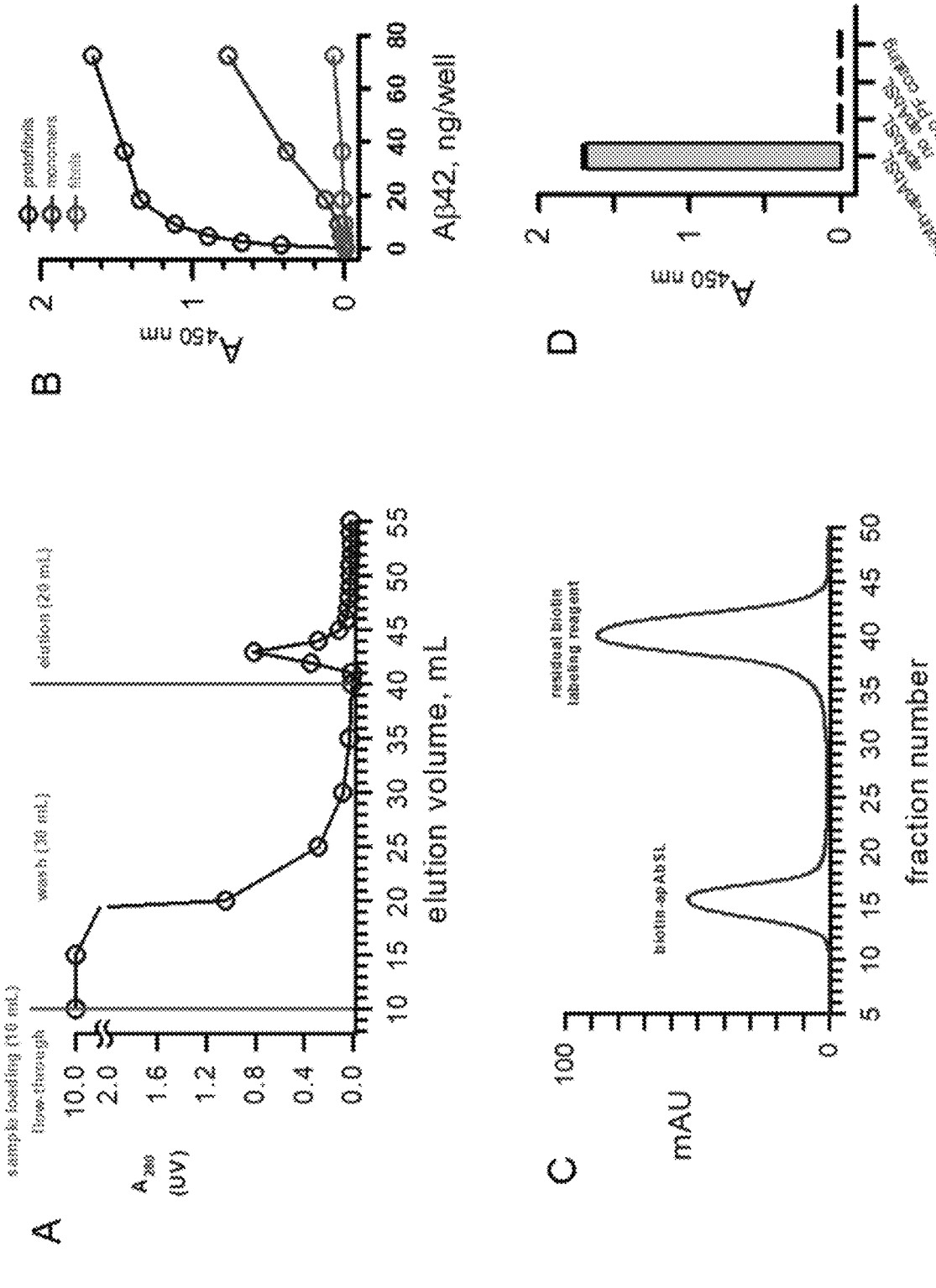
FIG. 7 shows the affinity purification and biotinylation of AbSL. Panel A shows the absorbance measured for each wash and elution volume collected from an Aβ42 protofibril conjugated resin column. Panel B shows the fluorescence results of an indirect ELISA showing selectivity of affinity purified AbSL (apAbSL) for Aβ42 protofibrils (blue) over monomers (red) or fibrils (green). Panel C depicts the SEC separation of biotinylated apAbSL from residual biotin labeling reagent. Panel D depicts absorbance detected using streptavidin-HRP and colorimetric analysis in ELISA wells coated with Aβ42 protofibrils and treated with biotinylated or non-biotinylated antibodies. Absorbance was only observed for the biotinylated apAbSL, confirming the labeling.

AbSL antiserum was purified on an Aβ42 protofibril conjugated resin using a column set-up and the elution spectrum is depicted in FIG. 7 panel A. The eluted affinity purified antibody (apAbSL) was tested for protofibril selectivity using the indirect ELISA assay described above, and showed strong selectivity over monomers and fibrils (FIG. 7 panel B). To test the effect of biotinylation on AbSL specificity, the apAbSL was incubated with N-hydroxysuccinimide ester (NHS)-PEG$_4$-biotin (ThermoFisher Scientific) and the reaction product purified by SEC (FIG. 7, panel C). ELISA wells were coated with Aβ42 protofibrils, incubated with unlabeled or biotinylated apAbSL, followed by detection with streptavidin-HRP and colorimetric analysis. Absorbance was only observed for the biotinylated apAbSL confirming successful labeling (FIG. 7, panel D).

Example 3: Generation and Characterization of Monoclonal Antibodies

Generation of Monoclonal AbSL (mAbSL)

For generation of monoclonal antibodies, isolated Aβ42 protofibrils were sent to Pacific Immunology (Ramona, CA) for immunization of rabbits as described above in Example 2. After testing of the serum for protofibril selectivity, splenocytes were transferred to ExonBio (San Diego, CA), and single B cells were isolated using biotinylated Aβ42 protofibrils. Isolated mRNA from heavy chain (HC) & light chain (LC) variable regions was converted into cDNA, and cloned into pRab293 HC and LC vectors, which contain rabbit IgG constant regions. Supernatants from small scale expression in 293-F cells were tested for protofibril affinity and selectivity (FIG. 8).

At least 60 supernatants were assessed by ELISA and monoclonal antibody (mAbSL) candidates were identified. Raw ELISA absorbance measured using the indirect ELISA assays described in Example 2 are shown in FIG. 8 panel A. The data were then normalized as a percentage of each antibody's protofibril recognition and shown in FIG. 8, panel B.

Figure 8:
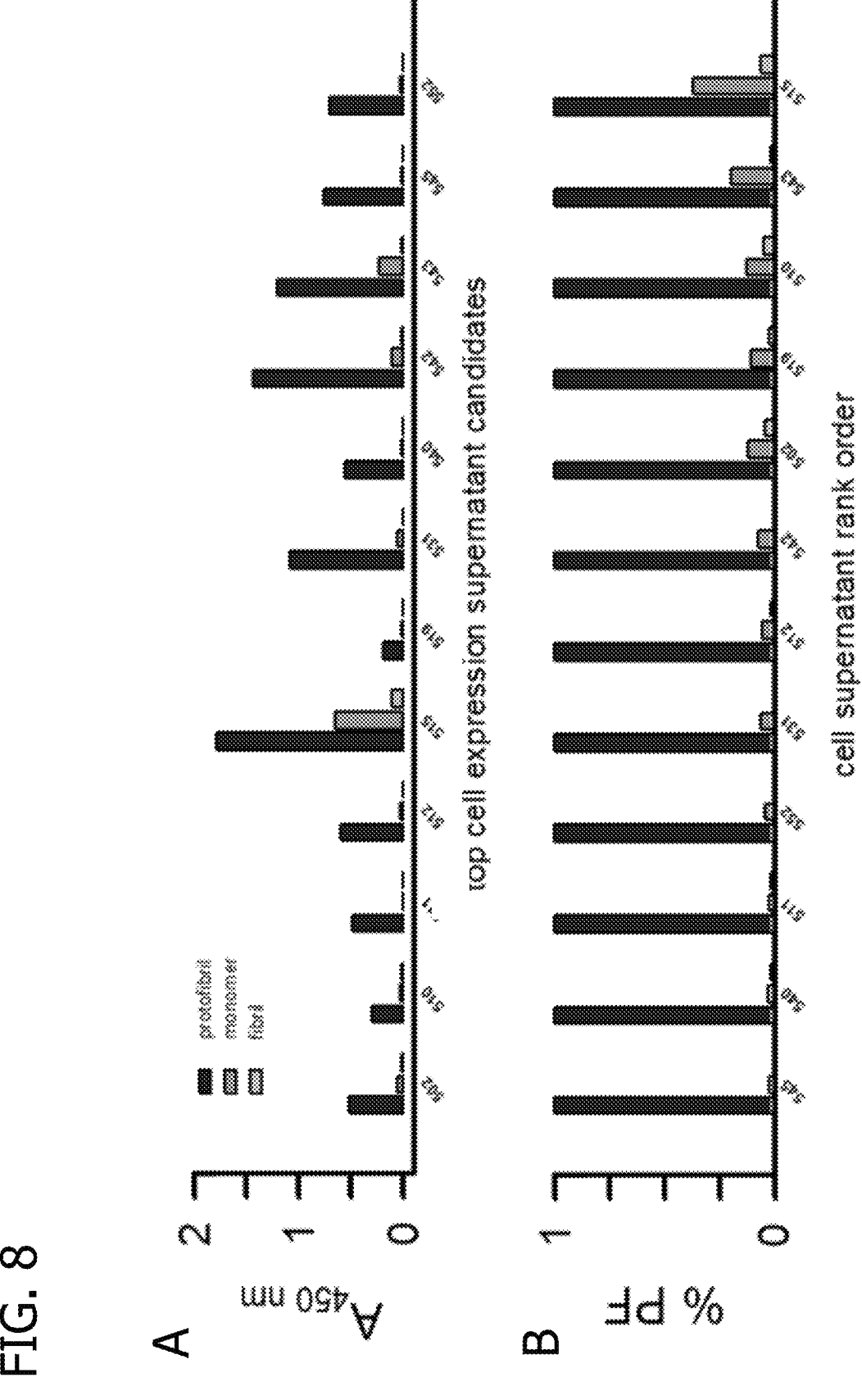
FIG. 8. Panel A shows the results of an ELISA assay testing the affinity for protofibrils, monomers or fibrils of different supernatants obtained from 293-F cells expressing heavy chain and light chain mRNA from isolated B cells from Aβ42 antiserum. Panel B shows the same data normalized as a percentage of each antibody's protofibril recognition.
Figure 9:
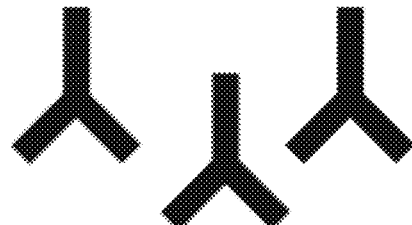
FIG. 9 depicts a diagram describing the steps taken to isolate, sequence and transfect the monoclonal antibodies described herein.
Figure 9:
Figure 9:
Figure 9:
Figure 9:
Figure 9:

The cells corresponding to the supernatants described in FIG. 8 were then developed according to the schematic in FIG. 9 to generate the monoclonal antibodies described herein. Briefly, assembled HC and LC DNA fragments from each mAbSL candidate was cloned as described above, transformed into DH5a bacterial cells, and grown in agar plates prepared in selective medium. Colonies were chosen and placed in a numbered grid agar plate. Colony PCR was conducted to verify insertion of DNA into vector. Positive colonies were amplified and the plasmid DNA purified by mini-prep. HC and LC plasmids were sequenced at Eurofins (Louisville, KY) and co-transfected into FREESTYLE 293-F cells (described below).

FreeStyle 293F Transfection

Figure 10:
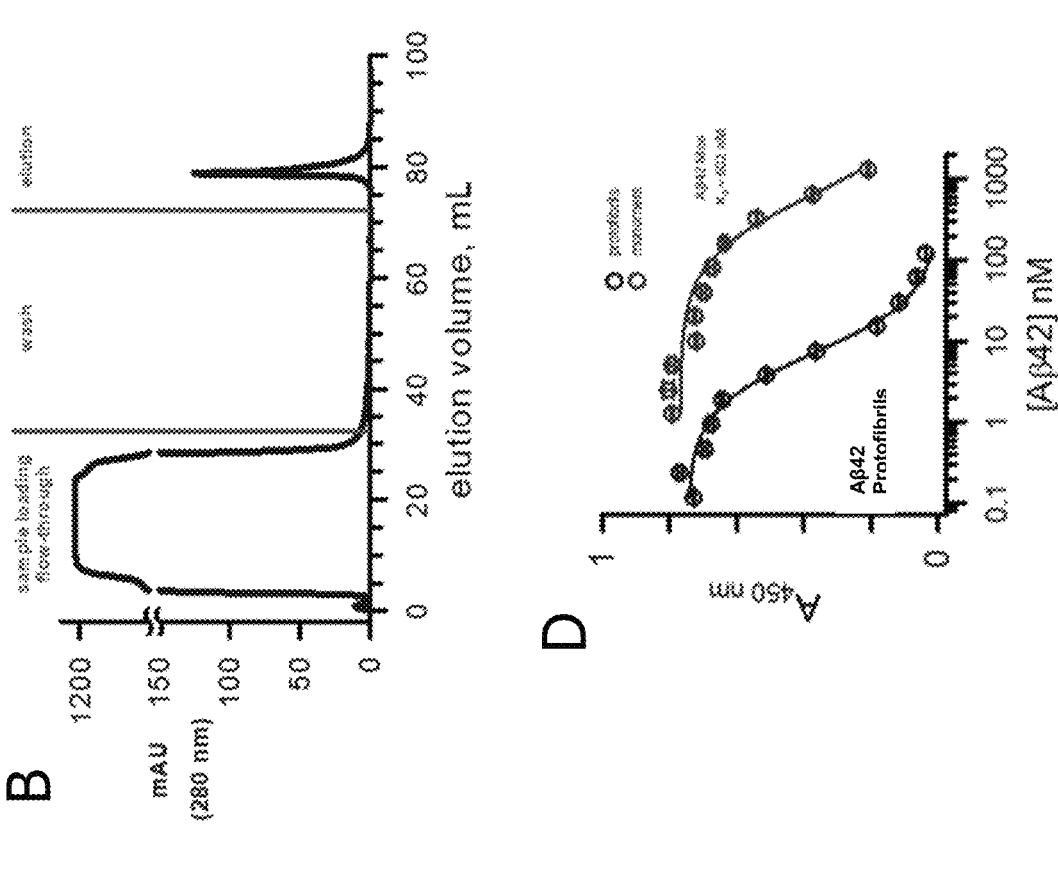
FIG. 10. Panel A is an immunodot blot of 293-F cell expression supernatants. Panel B depicts the fluorescence detected in various elution volumes from an affinity purification of the anti-Aβ42 monoclonal antibodies using a Protein G column. Panel C depicts the results of an indirect ELISA assay measuring the affinity of a monoclonal antibody (Ab-113) to Aβ42 protofibrils (blue), monomers (red) or fibrils (Green). Panel D depicts the results of a competition ELISA, as performed in panel D of FIG. 4, measuring the ability of protofibrils or monomers to compete with monoclonal antibody binding to wells coated with Aβ42 protofibrils.
Figure 10:
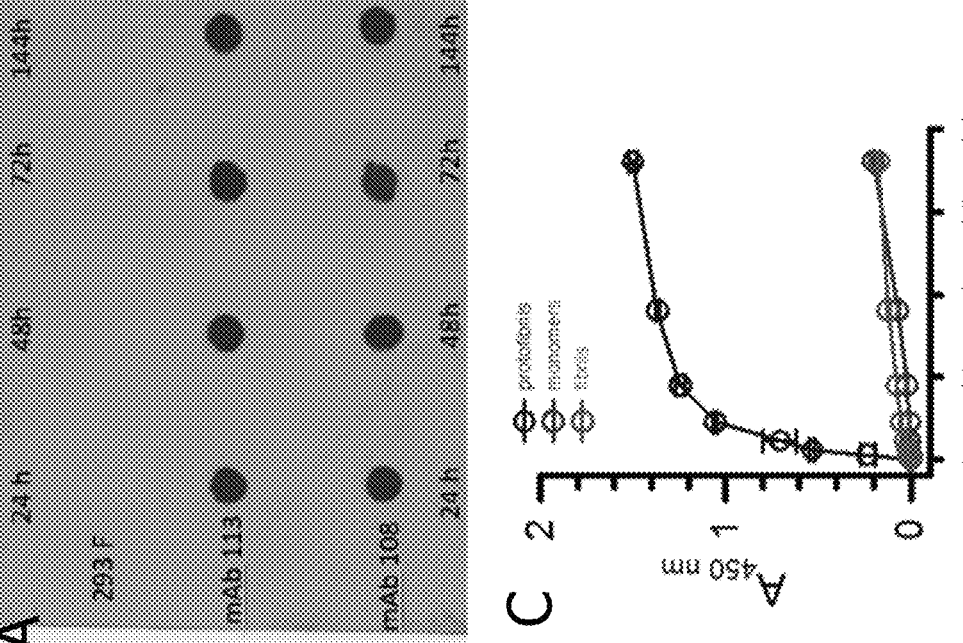

Briefly, 293-F cells were grown in suspension as per protocol in serum-free expression medium in sterile Erlenmeyer flasks under continuous rotation at 37° C. and 8% $CO_2$. Cells were co-transfected with HC & LC pRab293 plasmids using 293FECTIN (a cationic lipid-based formulation for transfecting DNA into eukaryotic cells) for DNA delivery in sterile 125 mL flasks (30 mL solution volume). Rabbit IgG was detected via immunodot blot (assay described below) in the medium for transfected 293-F cells, but not control cells, as soon as 24 h and remained constant through 144 h (FIG. 10, panel A). Cells were centrifuged and the cell expression medium supernatant (measured pH 7.3) was applied to a 5 mL Protein G affinity column using a large volume SUPERLOOP, washed with 8 column volumes, eluted with glycine buffer pH 1.85, and fractions immediately neutralized with Tris buffer (FIG. 10, panel B). Antibody concentration was determined before and after pooling and concentration using a 50 kD centrifugal filter.

Immunodot blot of 293-F cell expression supernatants. 2 µL of medium from untransfected 293-F cells and cells transfected with mAbSL113 or 108 was spotted on nitrocellulose, blocked, washed and probed with anti-rabbit IgG-HRP. Following addition of HRP ECL reagent, the membrane was exposed to film and developed.

Table 4 below depicts the various antibodies that were generated as described herein and the SEQ ID NOs of the heavy and light chains if known. Fifteen protofibril-selective antibodies and two nonselective antibodies were generated.

TABLE 4

| mAbSL | HC | LC |
|---|---|---|
| | Selective | |
| 108 | SEQ ID NO: 1 | SEQ ID NO: 2 |
| 113 | SEQ ID NO: 3 | SEQ ID NO: 4 |
| 502 | SEQ ID NO: 5 | SEQ ID NO: 6 |
| 510 | ND | ND |
| 511 | SEQ ID NO: 7 | SEQ ID NO: 8 |
| 512 | ND* | ND* |
| 515 | ND* | ND* |
| 519 | SEQ ID NO: 32 | SEQ ID NO: 33 |
| 531 | SEQ ID NO: 34 | SEQ ID NO: 9 |
| 540 | SEQ ID NO: 7* | SEQ ID NO: 8* |
| 542 | ND* | ND* |
| 543 | ND* | ND* |
| 545 | SEQ ID NO: 10 | SEQ ID NO: 11 |
| 552 | ND* | partial |
| | Non-selective | |
| 513 | SEQ ID NO: 12 | SEQ ID NO: 13 |
| 550 | SEQ ID NO: 14 | SEQ ID NO: 15 |

*ND: not yet determined.

Monoclonal AbSL (mAbSL) is Selective for Aβ Protofibrils 96-well ELISA plates were coated with varying amounts of Aβ42 protofibrils, Aβ42 monomers and (342 fibrils and analyzed by indirect ELISA with mAbSL 113 (0.5 µg/ml) and anti-rabbit IgG-HRP. The results of this indirect ELISA assay showed clear preference for Aβ42 protofibrils (FIG. 10, panel C). A competition ELISA was conducted as described above in Example 2. Wells were coated with 18 ng Aβ42 protofibrils and mAbSL 113 was incubated separately with increasing concentrations of Aβ42 protofibrils (blue) or Aβ42 monomers (red) prior to adding it to coated wells. Curve-fitting of the data yielded $K_D$ values for each antigen (FIG. 10, panel D). The affinity for Aβ42 protofibrils ($K_D$=7 nM) was an order of magnitude greater than that for monomers ($K_D$=602 nM). Error bars in panels C and D represent the standard error for triplicate measurements.

Detection of Protofibrillar Aβ in Human Cerebrospinal Fluid (CSF) Samples.

Figure 11:
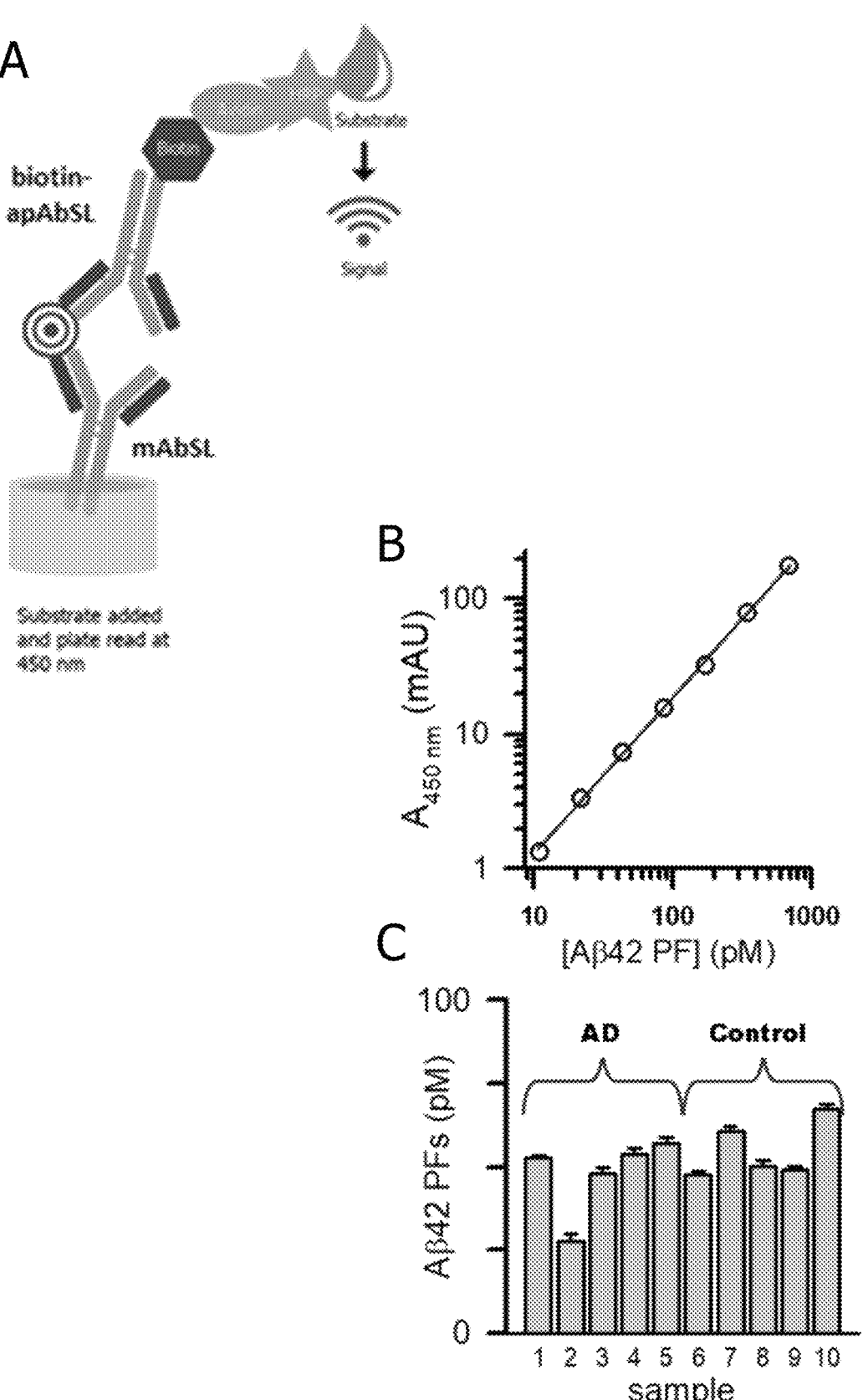
FIG. 11. Panel A shows a schematic of a sandwich ELISA used in this figure. Panel B is a standard curve showing that fluorescence is linearly proportional to increasing concentrations of Aβ42 protofibrils captured in the wells. Panel C shows the levels of Aβ protofibrils in human cerebrospinal fluid in Alzheimer's disease (AD) and control patients, quantified using the standard curve in Panel B.

A sensitive sandwich ELISA was developed using mAbSL as the capture antibody and biotinylated apAbSL as the detection antibody (see FIG. 11 panel A). In this assay, a single concentration of a capture antibody (that is, the monoclonal protofibril selective antibody) is added to a well. Increasing concentrations of protofibrils are added, bind to the capture Ab, and are detected by the biotinylated apAbSL antibody which can then be detected using streptavidin-HRP substrates. A standard curve was generated using known concentrations of protofibrils (FIG. 11, panel B) and was used to quantify levels of Aβ42 protofibrils in untested cerebrospinal fluid (CSF) samples. Specifically, human CSF from Alzheimer's Disease (AD) and control patients (n=3 each) was analyzed and the absorbance converted to pM Aβ protofibrils (PF) from the standard curve. Notably, the monoclonal antibodies were able to detect levels of Aβ42 protofibrils less than 100 pM, while the detection limit for Aβ monomers using the same assay is 200 pM (FIG. 11, panel C).

Conclusions

Antibody St. Louis (AbSL) is a conformation-selective antibody with a much higher affinity for protofibrillar Aβ42 compared to monomeric or fibrillar Aβ 42. AbSL detects pathological AD features that are distinct from those recognized by conventional Aβ antibodies. Monoclonal AbSL (mAbSL) and affinity-purified AbSL (apAbSL) sensitively detect protofibrillar Aβ in human CSF. Additional normalization factors are needed in human CSF to determine if protofibril levels are an AD indicator. A class of mAbSL antibodies have been cloned and sequenced. This will allow: (1) the investigation of AbSL residues that influence conformational selectivity for Aβ protofibrils, (2) probing of AbSL conformational epitope on Aβ protofibrils, and (3) determination of AbSL diagnostic/therapeutic efficacy.

Example 4: Epitope Determination of Monoclonal Antibodies

Figure 12:
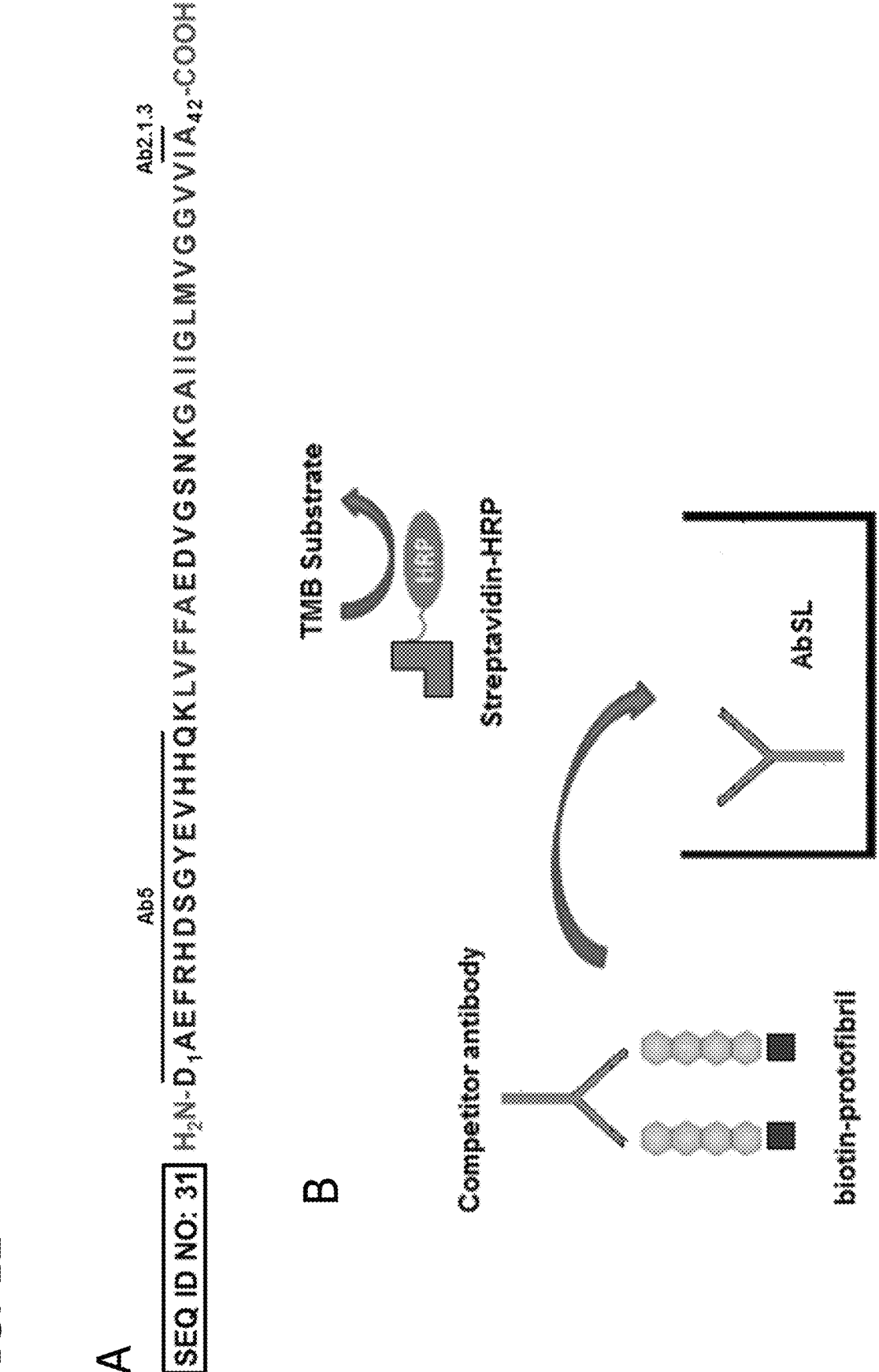
FIG. 12. Panel A shows the sequence of Aβ42 (SEQ ID NO: 31) with binding regions for Ab5 (a "N-terminal antibody") and Ab2.1.3 (a "C-terminal antibody") indicated. Panel B shows a schematic of the competition assay used to determine the general binding epitope of the antibodies. Briefly, biotinylated protofibrils were pre-incubated with concentrations of a competitor antibody (Ab5 or Ab2.1.3) before being added to a well coated with the inventive antibodies (e.g., AbSL). The absorbance detected (using Streptavidin-HRP) is proportional to the amount of protofibril that can still bind to the immobilized antibody.

Preliminary experiments were conducted to determine the binding epitope for the monoclonal and polyclonal antibodies generated in Examples 2 and 3. To do this, Aβ antibodies (Ab5 and Ab2.1.3) known to bind epitopes on the N-terminus and C terminus of Aβ42, respectively, were used to compete with the antibodies. FIG. 12 panel A shows the Aβ42 sequence (SEQ ID NO: 31) with the binding epitopes for Ab5 (N-terminus) and Ab2.1.3 (C-terminus) labeled. FIG. 12 panel B shows the competition assay used. Specifically, biotinylated protofibrils were pre-incubated with increasing concentrations of the competitor antibody prior to being added to a well coated with the monoclonal or polyclonal antibody. If the new antibody bound to an epitope that was shared by the competitor antibody, there would be less antibody binding in the well and consequently less signal generated by the Streptavidin-HRP.

Figure 13:
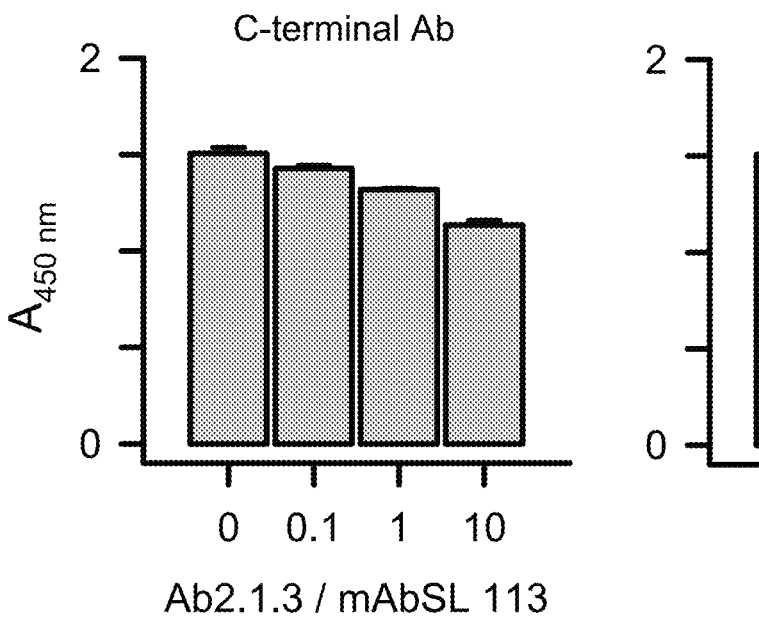
FIG. 13 shows the results of a competitive binding assay between a monoclonal antibody (mAbSL 113) and a C-terminal antibody (Ab 2.1.3, left panel) or a N-terminal antibody (Ab5, right panel).
Figure 13:
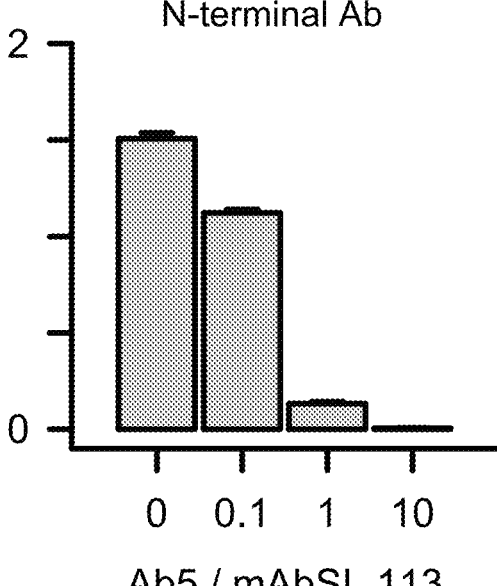

FIG. 13 shows the results of this competitive binding experiment for a monoclonal antibody (mAbSL 113). Specifically, this monoclonal antibody did not compete very well with the C-terminal antibody (left panel), but strongly competed with the N-terminal antibody (right panel). This suggests that the binding epitope for this monoclonal antibody is likely in the N-terminus of the Aβ42 peptide.

Figure 14:
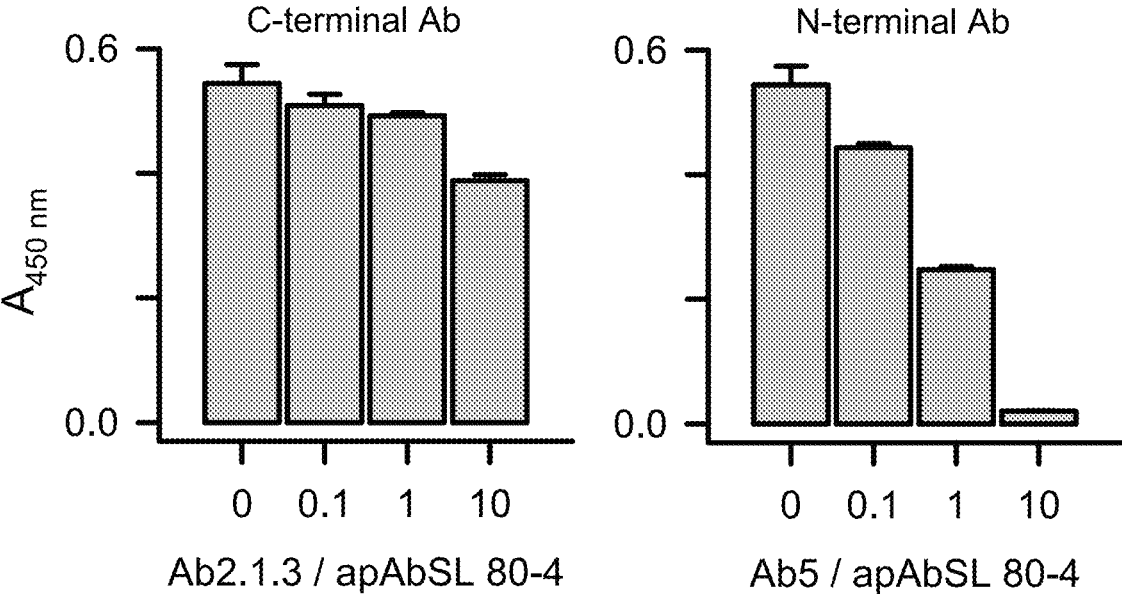
FIG. 14 shows the results of a competitive binding assay between a polyclonal affinity purified antibody (apAbSL 80-4) and a C-terminal antibody (Ab 2.1.3, left panel) or a N-terminal antibody (Ab5, right panel).

FIG. 14 shows the results of this competitive binding experiment for an affinity purified polyclonal antibody (apAbSL 80-4). Like the monoclonal antibody described above, this antibody also strongly competed with the N-terminal binding antibody (Ab5). This suggests that the polyclonal antibodies generated herein having a binding epitope in the N-terminal region of the Aβ42 peptide.

Example 5: Inhibition of AD Aggregation by Sub-Stoichiometric Amounts of AbSL Monoclonal Antibody Solutions of SEC-purified Aβ42 monomer (5 μM) were incubated quiescently at 37° C. (water bath) in low-retention tubes in the absence (circles) or presence of monoclonal AbSL (mAbSL 113) antibody at 0.01 (triangle) and 0.1 (diamonds) molar ratios to Aβ42. Thioflavin T (ThT) (10 μM) was included in the solution. Thioflavin T is a small molecule that gives strong fluorescence upon binding to amyloid fibrils, and can therefore be used to detect and quantify aggregation of Aβ. $NaN_3$ (0.05%) was also included in the solution to prevent microbial growth. At selected time points, ThT fluorescence was determined by placing 80 μL of the solution in a quartz cuvette and taking emission scans from 460-520 nm with an excitation wavelength of 450 nm. Numeric values were obtained by integration of the emission curves from 470-500 nm. The cuvette samples were recovered back into their respective tubes and incubated further.

Figure 15:
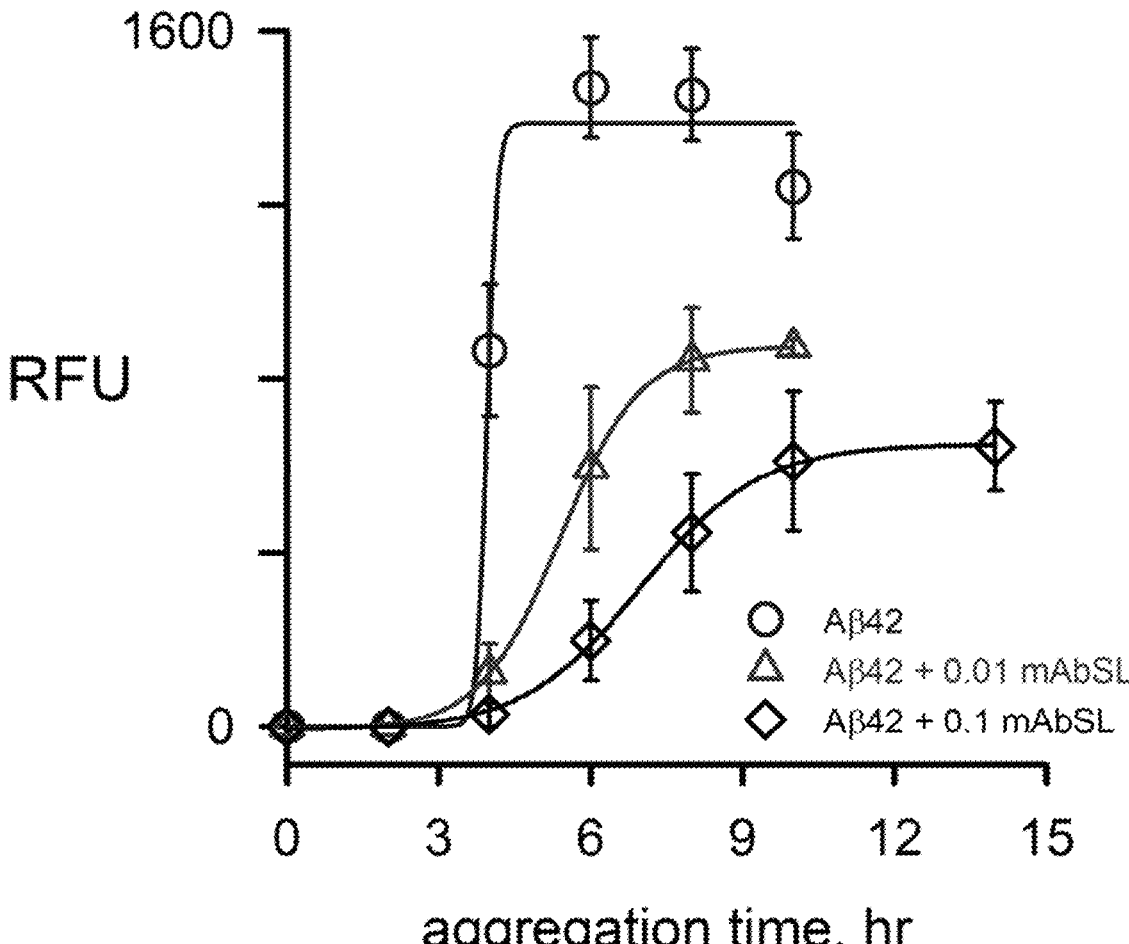
FIG. 15 provides the results for an assay showing that a monoclonal AbSL (mAbSL 113) inhibits Aβ aggregation at sub-stoichiometric ratios. Solutions of SEC-purified Aβ42 monomer (5 μM) were incubated quiescently at 37° C. in the absence (circles) or presence of monoclonal AbSL (mAbSL) antibody at 0.01 (triangle) and 0.1 (diamonds) molar ratios to Aβ42. Thioflavin T (ThT) (10 μM) was included in the solution. At selected time points, ThT fluorescence was determined by placing 80 μL of the solution in a quartz cuvette and taking emission scans from 460-520 nm with an excitation wavelength of 450 nm.

Results are shown in FIG. 15. Data points and error bars represent the average and standard error for n=3 replicate tubes at each time point for each aggregation solution. Curve fitting was done as described and yielded tin, values of 3.9 h, 5.4 h and 6.5 h for Aβ42 alone, Aβ42+0.01 mAbSL and Aβ42+0.1 mAbSL respectively. The data provided in FIG. 15 show that a monoclonal AbSL inhibited aggregation of Aβ42 monomer at substoichiometric ratios of antibody to Aβ42.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

REFERENCES

1. Selkoe. *Annu. Rev. Neurosci.,* 1994, 17. 489
2. Selkoe, *Nat Cell Biol,* 2004. 6. 1054
3. Glenner and Wong, *Biochem. Biophys. Res. Commun.,* 1984. 122, 1131
4. Suzuki et al., *Science,* 1994. 264, 1336
5. Hardy, *Trends Neurosci,* 1997, 20, 154
6. Jarrett et al., *Biochemistry,* 1993. 32. 4693
7. Gravina et al., *J Biol. Chem.,* 1995, 270, 7013
8. Lambert et al., *Proc. Natl Acad Sci USA,* 1998. 95. 6448
9. Kayed et al., *Science,* 2003, 300.486
10. Walsh et al., *J. Biol. Chem.,* 1997, 272, 22364
11. 1-larper et al., *Biochemistry,* 1999.38, 8972
12. Jan et al., *Nat Prowc,* 2010, 5, 1186
13. Walsh et al., *J. Biol. Chem.,* 1999, 274, 25945
14. Harper et al., *Chem. Biol.,* 1997, 4, 951
15. Westerman et al., *Neurosci.,* 2002, 22, 1858
16. Maass and Selkoe. *Nat Rev Mot Cell Biol,* 2007, 8, 101
17. Walsh and Selkoe, *J Neurochem,* 2007, 101, 1172
18. Walsh et al., *Nature,* 2002, 416, 535
19. Gong et al., *Proc. Natl. Acad. Sci, USA,* 2003, 100, 10417
20. Georganopoulou et al., *Proc. Natl. Acad. Sci. USA,* 2005, 102, 2273
21. Terry et al. *Am. J, Pathol.,* 1964, 44, 269
22. Koffie et al., *Proc Nat! Acad Sci USA,* 2009, 106, 4012
23. Harper et al., *Chem. Biol.,* 1997, 4, 119
24. Kheterpal et al., *Biochemistry,* 2003, 42, 14092
25. Ye et al., *Neurobiol Dis,* 2003. 13, 177
26. O'Nuallain et al., *J Neurosei.* 2010. 30. 14411
27. Paranjape et al., *ACS Chem Neurosci,* 2012, 3, 302

What is claimed is:

1. An antibody or antigen-binding fragment thereof having affinity for amyloid beta (Aβ) protofibrils comprising one of:

an immunoglobulin heavy chain variable region comprising an amino acid sequence comprising SEQ ID NO: 1 and an immunoglobulin light chain variable region comprising an amino acid sequence comprising SEQ ID NO: 2;

an immunoglobulin heavy chain variable region comprising an amino acid sequence comprising SEQ ID NO: 3 and an immunoglobulin light chain variable region comprising an amino acid sequence comprising SEQ ID NO: 4;

an immunoglobulin heavy chain variable region comprising an amino acid sequence comprising SEQ ID NO: 5 and an immunoglobulin light chain variable region comprising an amino acid sequence comprising SEQ ID NO: 6;

an immunoglobulin heavy chain variable region comprising an amino acid sequence comprising SEQ ID NO: 7 and an immunoglobulin light chain variable region comprising an amino acid sequence comprising SEQ ID NO: 8;

an immunoglobulin heavy chain variable region comprising an amino acid sequence comprising SEQ ID NO: 10 and an immunoglobulin light chain variable region comprising an amino acid sequence comprising SEQ ID NO: 11;

an immunoglobulin heavy chain variable region comprising an amino acid sequence comprising SEQ ID NO: 32 and an immunoglobulin light chain variable region comprising an amino acid sequence comprising SEQ ID NO: 33; or an immunoglobulin heavy chain variable region com-
prises an amino acid sequence comprising SEQ ID NO:
34 and an immunoglobulin light chain variable region
comprising an amino acid sequence comprising SEQ
ID NO: 9.

2. A nucleic acid comprising a nucleotide sequence
encoding an immunoglobulin heavy chain variable region,
wherein the nucleotide sequence is selected from the group
consisting of SEQ ID NOs: 16, 18, 20, 22, 25, 35, 37, 27, and
29.

3. The nucleic acid of claim 2, comprising a nucleotide
sequence comprising any one of SEQ ID NOs: 16, 18, 20,
22, 25, 35, and 37.

4. A nucleic acid comprising a nucleotide sequence
encoding an immunoglobulin light chain variable region,
wherein the nucleotide sequence is selected from the group
consisting of SEQ ID NOs: 17, 19, 21, 23, 24, 26, 36, 28, and
30.

5. The nucleic acid of claim 4, comprising a nucleotide
sequence comprising any one of SEQ ID NOs: 17, 19, 21,
23, 24, 26, and 36.

* * * * *

SEQUENCE LISTING

<160> NUMBER OF SEQ ID NOS: 37

<210> SEQ ID NO 1
<211> LENGTH: 138
<212> TYPE: PRT

<213> ORGANISM: Artificial Sequence
<220> FEATURE:
<223> OTHER INFORMATION: Synthetic construct

<400> SEQUENCE: 1

```
Lys Gly Val Gln Cys Gln Ser Leu Glu Glu Ser Arg Gly Gly Leu Phe
1               5                   10                  15

Lys Pro Thr Asp Thr Leu Thr Leu Thr Cys Thr Val Ser Gly Ile Asp
            20                  25                  30

Leu Ser Ser Asn Ser Met Ser Trp Val Arg Gln Ala Pro Gly Asn Gly
        35                  40                  45

Leu Glu Trp Ile Gly Phe Ile Trp Ser Gly Gly Asn Thr Asp Tyr Ala
    50                  55                  60

Asn Trp Ala Lys Ser Arg Ser Thr Ile Thr Arg Asn Thr Asn Leu Asn
65                  70                  75                  80

Thr Val Thr Leu Lys Met Thr Ser Leu Thr Ala Ala Asp Thr Ala Thr
                85                  90                  95

Tyr Phe Cys Ala Arg Trp His Pro Asp Tyr Lys Thr Phe Asn Ile Trp
            100                 105                 110

Gly Pro Gly Thr Leu Val Thr Val Ser Ser Gly Gln Pro Lys Ala Pro
        115                 120                 125

Ser Val Phe Pro Gln Ala Pro Cys Cys Gly
        130                 135
```

<210> SEQ ID NO 2
<211> LENGTH: 124
<212> TYPE: PRT
<213> ORGANISM: Artificial Sequence
<220> FEATURE:
<223> OTHER INFORMATION: Synthetic construct

<400> SEQUENCE: 2

```
Leu Pro Gly Ala Thr Phe Ala Ile Val Met Thr Gln Thr Pro Ser Ser
1               5                   10                  15

Lys Ser Val Pro Val Gly Asp Thr Val Thr Ile Asn Cys Gln Ala Ser
            20                  25                  30

Glu Ser Val Tyr Gly Asn Asn Arg Leu Ala Trp Phe Gln Gln Lys Pro
        35                  40                  45

Gly Gln Pro Pro Lys Leu Leu Ile Tyr Leu Ala Ser Asn Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Val Cys Asp Asp Ala Ala Thr Tyr Tyr Cys
                85                  90                  95

Gly Gly Tyr Lys Ser Ser Thr Gly Asp Asp Leu Ala Phe Gly Gly Gly
            100                 105                 110

Thr Glu Val Val Val Lys Gly Asp Pro Val Ala Pro
        115                 120
```

<210> SEQ ID NO 3
<211> LENGTH: 138
<212> TYPE: PRT
<213> ORGANISM: Artificial Sequence
<220> FEATURE:
<223> OTHER INFORMATION: Synthetic construct

<400> SEQUENCE: 3

```
Lys Gly Val Gln Cys Gln Ser Leu Glu Glu Ser Gly Gly Gly Leu Val
1               5                   10                  15
```

```
Lys Pro Gly Ala Ser Leu Thr Leu Thr Cys Ala Ala Ser Gly Phe Ser
            20                  25                  30

Phe Ser Ser Gly Tyr Asp Met Cys Trp Val Arg Gln Ala Pro Gly Lys
            35                  40                  45

Gly Leu Glu Trp Ile Ala Cys Ile Gly Ile Pro Ser Gly Ser Thr Trp
        50                  55                  60

Tyr Ala Ser Trp Ala Lys Gly Arg Phe Thr Ile Ser Lys Thr Ser Ser
65                  70                  75                  80

Thr Thr Val Thr Leu Gln Met Thr Ser Leu Thr Ala Ala Asp Thr Ala
                85                  90                  95

Thr Tyr Phe Cys Ala Arg Arg Gly Thr Gly Asn Asn Trp Gly Leu Trp
            100                 105                 110

Gly Pro Gly Thr Leu Val Thr Val Ser Ser Gly Gln Pro Lys Ala Pro
        115                 120                 125

Ser Val Phe Pro Leu Ala Pro Cys Cys Gly
    130                 135
```

```
<210> SEQ ID NO 4
<211> LENGTH: 124
<212> TYPE: PRT
<213> ORGANISM: Artificial Sequence
<220> FEATURE:
<223> OTHER INFORMATION: Synthetic construct

<400> SEQUENCE: 4
```

```
Leu Pro Gly Ala Thr Phe Ala Ile Val Met Thr Gln Thr Pro Ser Ser
1               5                   10                  15

Lys Ser Val Pro Val Gly Asp Thr Val Thr Ile Asn Cys Gln Ala Ser
            20                  25                  30

Glu Ser Val Tyr Ser Asn Asn Arg Leu Ala Trp Phe Arg Gln Lys Pro
            35                  40                  45

Gly Gln Pro Pro Lys Leu Leu Ile Tyr Tyr Ala Ser Thr Leu Ala Ser
        50                  55                  60

Gly Val Pro Ser Arg Phe Lys Gly Ser Gly Ser Gly Thr Gln Phe Thr
65                  70                  75                  80

Leu Thr Ile Ser Asp Val Val Cys Asp Asp Ala Ala Thr Tyr Tyr Cys
                85                  90                  95

Ala Gly Tyr Lys Ser Ala Ser Ile Asp Gly Asp Ala Phe Gly Gly Gly
            100                 105                 110

Thr Glu Val Val Val Lys Gly Asp Pro Val Ala Pro
        115                 120
```

```
<210> SEQ ID NO 5
<211> LENGTH: 139
<212> TYPE: PRT
<213> ORGANISM: Artificial Sequence
<220> FEATURE:
<223> OTHER INFORMATION: Synthetic construct

<400> SEQUENCE: 5
```

```
Lys Gly Val Gln Cys Gln Gln Gln Leu Val Glu Ser Gly Gly Gly Leu
1               5                   10                  15

Val Lys Pro Gly Ala Ser Leu Thr Leu Thr Cys Thr Ala Ser Gly Phe
            20                  25                  30

Ser Phe Ser Ser Gly Ser Asp Met Cys Trp Val Arg Gln Pro Pro Gly
            35                  40                  45

Lys Gly Leu Glu Trp Ile Ala Cys Ile Gly Ile Ser Ser Gly Ser Thr
```

-continued

```
          50                  55                  60

Tyr Tyr Ala Asn Trp Ala Lys Gly Arg Phe Thr Ile Ser Lys Thr Ser
65                  70                  75                  80

Ser Thr Thr Val Thr Leu Gln Met Thr Ser Leu Thr Ala Ala Asp Thr
                85                  90                  95

Ala Thr Tyr Phe Cys Ala Arg Ala Ile Gly Pro Phe His Phe Asn Leu
                100                 105                 110

Trp Gly Pro Gly Thr Leu Val Thr Val Ser Ser Gly Gln Pro Lys Ala
        115                 120                 125

Pro Ser Val Phe Pro Leu Ala Pro Cys Cys Gly
    130                 135

<210> SEQ ID NO 6
<211> LENGTH: 124
<212> TYPE: PRT
<213> ORGANISM: Artificial Sequence
<220> FEATURE:
<223> OTHER INFORMATION: Synthetic construct

<400> SEQUENCE: 6

Leu Pro Gly Ala Thr Phe Ala Ile Val Met Thr Gln Thr Pro Ser Ser
1               5                   10                  15

Lys Ser Val Pro Val Gly Asp Thr Val Thr Ile Asn Cys Gln Ala Ser
                20                  25                  30

Glu Ser Val Tyr Ser Asn Asn Arg Leu Ala Trp Tyr Gln Gln Lys Pro
                35                  40                  45

Gly Gln Pro Pro Lys Leu Leu Ile Tyr Gly Ala Ser Thr Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Val Cys Asp Asp Ala Ala Thr Tyr Tyr Cys
                85                  90                  95

Ala Gly Tyr Lys Ser Gly Ile Gly Asp Gly Ile Ala Phe Gly Gly Gly
                100                 105                 110

Thr Glu Val Val Val Lys Gly Asp Pro Val Ala Pro
        115                 120

<210> SEQ ID NO 7
<211> LENGTH: 138
<212> TYPE: PRT
<213> ORGANISM: Artificial Sequence
<220> FEATURE:
<223> OTHER INFORMATION: Synthetic construct

<400> SEQUENCE: 7

Lys Gly Val Gln Cys Gln Ser Leu Glu Glu Ser Gly Gly Asp Leu Val
1               5                   10                  15

Lys Pro Glu Gly Ser Leu Thr Leu Thr Cys Thr Ala Ser Gly Phe Ser
                20                  25                  30

Phe Ser Thr Asn Tyr Asp Met Cys Trp Val Arg Gln Ala Pro Gly Lys
                35                  40                  45

Gly Leu Glu Trp Ile Ala Cys Val Gly Ala Gly Ser Gly Ser Thr Tyr
    50                  55                  60

Tyr Ala Ser Trp Ala Lys Gly Arg Phe Thr Ile Ser Lys Thr Ser Ser
65                  70                  75                  80

Thr Thr Val Thr Leu Gln Met Thr Ser Leu Thr Ala Ala Asp Thr Ala
                85                  90                  95
```

-continued

```
Thr Tyr Phe Cys Ala Arg Trp Thr Ser Gly Leu Tyr Ile Asn Phe Trp
                100                 105                 110

Gly Pro Gly Thr Leu Val Thr Val Ser Ser Gly Gln Pro Lys Ala Pro
        115                 120                 125

Ser Val Phe Pro Leu Ala Pro Cys Cys Gly
    130                 135

<210> SEQ ID NO 8
<211> LENGTH: 124
<212> TYPE: PRT
<213> ORGANISM: Artificial Sequence
<220> FEATURE:
<223> OTHER INFORMATION: Synthetic construct

<400> SEQUENCE: 8

Leu Pro Gly Ala Thr Phe Ala Ile Val Met Thr Gln Thr Pro Ser Ser
1               5                   10                  15

Lys Ser Val Pro Val Gly Asp Thr Val Thr Ile Asn Cys Gln Ala Ser
            20                  25                  30

Glu Ser Val Tyr Ser Asn Asn Arg Leu Ala Trp Phe Gln Gln Lys Pro
        35                  40                  45

Gly Gln Pro Pro Lys Leu Leu Ile Tyr Leu Ala Ser Thr Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Val Cys Asp Asp Ala Ala Thr Tyr Tyr Cys
                85                  90                  95

Thr Gly Tyr Lys Ser Ser Asn Thr Asp Gly Ile Gly Phe Gly Gly Gly
                100                 105                 110

Thr Glu Val Val Val Lys Gly Asp Pro Val Ala Pro
        115                 120

<210> SEQ ID NO 9
<211> LENGTH: 124
<212> TYPE: PRT
<213> ORGANISM: Artificial Sequence
<220> FEATURE:
<223> OTHER INFORMATION: Synthetic construct

<400> SEQUENCE: 9

Leu Pro Gly Ala Thr Phe Ala Ile Val Met Thr Gln Thr Pro Ser Ser
1               5                   10                  15

Lys Ser Val Pro Val Gly Asp Thr Val Thr Ile Ser Cys Gln Ala Ser
            20                  25                  30

Glu Ser Val Tyr Ser Asn Asn Arg Leu Ala Trp Phe Gln Gln Lys Pro
        35                  40                  45

Gly Gln Pro Pro Lys Leu Leu Ile Tyr Leu Ala Ser Thr Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Val Cys Asp Asp Ala Ala Thr Tyr Tyr Cys
                85                  90                  95

Ala Gly Tyr Lys Ile Ser Asn Thr Asp Gly Ile Gly Phe Gly Gly Gly
                100                 105                 110

Thr Glu Val Val Val Lys Gly Asp Pro Val Ala Pro
        115                 120

<210> SEQ ID NO 10
```

```
<211> LENGTH: 139
<212> TYPE: PRT
<213> ORGANISM: Artificial Sequence
<220> FEATURE:
<223> OTHER INFORMATION: Synthetic construct

<400> SEQUENCE: 10

Lys Gly Val Gln Cys Gln Gln Gln Leu Val Glu Ser Gly Gly Gly Leu
1               5                   10                  15

Val Lys Pro Gly Ala Ser Leu Thr Leu Thr Cys Lys Ala Ser Arg Phe
            20                  25                  30

Ser Phe Ser Ser Ala Tyr Asp Met Gly Trp Val Arg Gln Ala Pro Gly
        35                  40                  45

Lys Gly Leu Glu Trp Ile Ala Cys Ile Gly Ser Ser Ser Gly Thr Thr
    50                  55                  60

Tyr Tyr Ala Ser Trp Ala Lys Gly Arg Phe Thr Ile Ser Lys Thr Ser
65                  70                  75                  80

Ser Thr Thr Val Thr Leu Gln Met Thr Ser Leu Thr Ala Ala Asp Thr
                85                  90                  95

Ala Thr Tyr Phe Cys Ala Arg Ala Gln Ser Pro Phe His Phe Asn Leu
            100                 105                 110

Trp Gly Pro Gly Thr Leu Val Ala Val Ser Ser Gly Gln Pro Lys Ala
            115                 120                 125

Pro Ser Val Phe Pro Leu Ala Pro Cys Cys Gly
    130                 135

<210> SEQ ID NO 11
<211> LENGTH: 124
<212> TYPE: PRT
<213> ORGANISM: Artificial Sequence
<220> FEATURE:
<223> OTHER INFORMATION: Synthetic construct

<400> SEQUENCE: 11

Leu Pro Gly Ala Thr Phe Ala Ile Val Met Thr Gln Thr Pro Ser Ser
1               5                   10                  15

Lys Ser Val Pro Val Gly Asp Thr Val Thr Ile Asn Cys Gln Ala Ser
            20                  25                  30

Glu Ser Val Tyr Ser Asn Asn Arg Leu Ala Trp Tyr Gln Gln Lys Pro
        35                  40                  45

Gly Gln Pro Pro Lys Leu Leu Ile Tyr Gly Ala Ser Thr Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Val Cys Asp Asp Ala Ala Thr Tyr Tyr Cys
                85                  90                  95

Ala Gly Tyr Lys Ser Ser Ser Thr Asp Gly Phe Ala Phe Gly Gly Gly
            100                 105                 110

Thr Glu Val Val Val Lys Gly Asp Pro Val Ala Pro
            115                 120

<210> SEQ ID NO 12
<211> LENGTH: 139
<212> TYPE: PRT
<213> ORGANISM: Artificial Sequence
<220> FEATURE:
<223> OTHER INFORMATION: Synthetic construct

<400> SEQUENCE: 12
```

-continued

```
Lys Gly Val Gln Cys Gln Gln Gln Leu Val Glu Ser Gly Gly Gly Leu
1               5                   10                  15

Val Lys Pro Gly Ala Ser Leu Thr Leu Thr Cys Thr Ala Ser Gly Phe
            20                  25                  30

Ser Phe Ser Arg Tyr Ser Asp Met Cys Trp Val Arg Gln Pro Pro Gly
            35                  40                  45

Lys Gly Leu Glu Trp Ile Ala Cys Ile Gly Ile Ser Ser Gly Thr Thr
        50                  55                  60

Tyr Tyr Ala Ser Trp Ala Lys Gly Arg Phe Thr Ile Ser Lys Thr Ser
65                  70                  75                  80

Ser Thr Thr Val Thr Leu Gln Met Thr Ser Leu Thr Ala Ala Asp Thr
                85                  90                  95

Ala Thr Tyr Leu Cys Thr Arg Ala Ile Gly Pro Phe His Phe Asn Leu
                100                 105                 110

Trp Gly Pro Gly Thr Leu Val Thr Val Ser Ser Gly Gln Pro Lys Ala
            115                 120                 125

Pro Ser Val Phe Pro Leu Ala Pro Cys Cys Gly
        130                 135
```

```
<210> SEQ ID NO 13
<211> LENGTH: 124
<212> TYPE: PRT
<213> ORGANISM: Artificial Sequence
<220> FEATURE:
<223> OTHER INFORMATION: Synthetic construct

<400> SEQUENCE: 13
```

```
Leu Pro Gly Ala Thr Phe Ala Ile Val Met Thr Gln Thr Pro Ser Ser
1               5                   10                  15

Arg Ser Val Pro Val Gly Asp Thr Val Thr Ile Ser Cys Gln Ala Ser
            20                  25                  30

Glu Ser Val Tyr Asn Asn Asn Arg Leu Ala Trp Tyr Gln Gln Lys Ala
            35                  40                  45

Gly Gln Pro Pro Lys Leu Leu Ile Tyr Gly Ala Ser Thr Leu Ala Ser
        50                  55                  60

Gly Val Pro Ser Arg Phe Lys Gly Ser Gly Ser Gly Thr Gln Phe Thr
65                  70                  75                  80

Leu Thr Ile Ser Asp Val Val Cys Asp Asp Ala Ala Thr Tyr Tyr Cys
                85                  90                  95

Ala Gly Tyr Lys Ser Gly Ser Thr Asp Gly Cys Ala Phe Gly Gly Gly
                100                 105                 110

Thr Glu Val Val Val Lys Gly Asp Pro Val Ala Pro
            115                 120
```

```
<210> SEQ ID NO 14
<211> LENGTH: 139
<212> TYPE: PRT
<213> ORGANISM: Artificial Sequence
<220> FEATURE:
<223> OTHER INFORMATION: Synthetic construct

<400> SEQUENCE: 14
```

```
Lys Gly Val Gln Cys Gln Gln Gln Leu Val Glu Ser Gly Gly Gly Leu
1               5                   10                  15

Val Lys Pro Gly Ala Ser Leu Thr Leu Thr Cys Thr Ala Ser Gly Phe
            20                  25                  30

Ser Phe Ser Arg Asp Ser Asp Met Cys Trp Val Arg Gln Pro Pro Gly
            35                  40                  45
```

```
Lys Gly Leu Glu Trp Ile Ala Cys Ile Gly Ile Ser Ser Gly Ile Thr
    50                  55                  60

Tyr Tyr Ala Asn Trp Ala Arg Gly Arg Phe Thr Ile Ser Lys Thr Ser
65                  70                  75                  80

Ser Thr Thr Val Thr Leu Gln Met Thr Ser Leu Thr Ala Ala Asp Thr
                85                  90                  95

Ala Thr Tyr Phe Cys Ala Arg Ala Ile Gly Pro Phe His Phe Asn Leu
                100                 105                 110

Trp Gly Pro Gly Thr Leu Val Thr Val Ser Ser Gly Gln Pro Lys Ala
            115                 120                 125

Pro Ser Val Phe Pro Leu Ala Pro Cys Cys Gly
    130                 135
```

```
<210> SEQ ID NO 15
<211> LENGTH: 124
<212> TYPE: PRT
<213> ORGANISM: Artificial Sequence
<220> FEATURE:
<223> OTHER INFORMATION: Synthetic construct

<400> SEQUENCE: 15
```

```
Leu Pro Gly Ala Thr Phe Ala Ile Val Met Thr Gln Thr Pro Ser Ser
1                   5                   10                  15

Lys Ser Val Pro Val Gly Asp Thr Val Thr Ile Asp Cys Gln Ala Ser
                20                  25                  30

Glu Ser Val Tyr Ser Lys Asn Arg Leu Ala Trp Tyr Gln Gln Lys Pro
            35                  40                  45

Gly Gln Pro Pro Lys Leu Leu Ile Tyr Gly Ala Ser Thr Leu Ala Ser
    50                  55                  60

Gly Val Pro Ser Arg Phe Lys Gly Ser Gly Ser Gly Thr Gln Phe Thr
65                  70                  75                  80

Leu Thr Val Ser Asp Val Val Cys Asp Asp Ala Ala Thr Tyr Tyr Cys
                85                  90                  95

Ala Gly Tyr Lys Ser Gly Ile Gly Asp Gly Ile Ala Phe Gly Gly Gly
            100                 105                 110

Thr Glu Val Val Val Lys Gly Asp Pro Val Ala Pro
    115                 120
```

```
<210> SEQ ID NO 16
<211> LENGTH: 415
<212> TYPE: DNA
<213> ORGANISM: Artificial Sequence
<220> FEATURE:
<223> OTHER INFORMATION: Synthetic construct

<400> SEQUENCE: 16
```

```
aaaggtgtcc agtgtcagtc gctggaggag tccaggggag gtctcttcaa gccaacggat      60
accctgacac tcacctgcac agtctctgga atcgacctca gtagtaattc aatgagctgg     120
gtccgccagg ctccagggaa cggcctggag tggatcggat tcatttggag tggtggtaac     180
acagactatg cgaactgggc gaaaagccga tccaccatca ccagaaacac caacctgaac     240
acggtgactc tgaaaatgac cagtctgaca gccgcggaca cggccaccta tttctgtgcg     300
agatggcatc ctgattataa aactttttaac atctggggcc caggcaccct ggtcaccgtc     360
tcctcagggc aacctaaggc tccatcagtc ttcccacagg cccctgctg cgggg          415
```

```
<210> SEQ ID NO 17
```

-continued

```
<211> LENGTH: 373
<212> TYPE: DNA
<213> ORGANISM: Artificial Sequence
<220> FEATURE:
<223> OTHER INFORMATION: Synthetic construct

<400> SEQUENCE: 17
gctcccaggt gccacatttg ccatcgtgat gacccagact ccatcttcca agtctgtccc      60
tgtgggagac acagtcacca tcaattgcca ggccagtgag agtgtttatg gtaacaaccg     120
cttagcctgg tttcaacaga aaccagggca gcctcccaag ctcctgatct atctggcatc     180
caatctggca tctggggtcc catcgcggtt caaaggcagt ggatctggga cacagttcac     240
tctcaccatc agcgatgtgg tgtgtgacga tgctgccact tactactgtg gaggatataa     300
aagtagtact ggtgatgatt tagctttcgg cggagggacc gaggtggtgg tcaaaggtga     360
tccagttgca cct                                                        373

<210> SEQ ID NO 18
<211> LENGTH: 415
<212> TYPE: DNA
<213> ORGANISM: Artificial Sequence
<220> FEATURE:
<223> OTHER INFORMATION: Synthetic construct

<400> SEQUENCE: 18
aaaggtgtcc agtgtcagtc gttggaggag tccgggggag gcctggtcaa gcctggggca      60
tccctgacac tcacctgcgc agcctctgga ttctccttca gtagcggcta cgacatgtgc     120
tgggtccgcc aggctccagg gaaggggctg gagtggatcg catgcattgg tattcctagt     180
ggtagcacat ggtacgcgag ctgggcgaaa ggccgattca ccatctccaa aacctcgtcg     240
accacggtga ctctgcaaat gaccagtctg acagccgcgg acacggccac ctatttctgt     300
gcgagacgtg gtactggtaa taattggggc ttgtggggcc caggcaccct ggtcacggtc     360
tcctcagggc aacctaaggc tccatcagtc ttcccactgg cccccctgctg cgggg          415

<210> SEQ ID NO 19
<211> LENGTH: 373
<212> TYPE: DNA
<213> ORGANISM: Artificial Sequence
<220> FEATURE:
<223> OTHER INFORMATION: Synthetic construct

<400> SEQUENCE: 19
gctcccaggt gccacatttg ccatcgtgat gacccagact ccatcttcca agtctgtccc      60
tgtgggagac acagtcacca tcaattgcca ggccagtgag agtgtttata gtaacaaccg     120
cttagcctgg tttcgacaga aaccagggca gcctcccaag ctcctgatct attatgcatc     180
cactctggca tctggggtcc cttcgcggtt caaaggcagt ggatctggga cacagttcac     240
tctcaccatc agtgatgtgg tgtgtgacga tgctgccact tactactgtg caggatataa     300
aagtgctagc attgatggtg atgctttcgg cggagggacc gaggtggtgg tcaaaggtga     360
tccagttgca cct                                                        373

<210> SEQ ID NO 20
<211> LENGTH: 418
<212> TYPE: DNA
<213> ORGANISM: Artificial Sequence
<220> FEATURE:
<223> OTHER INFORMATION: Synthetic construct

<400> SEQUENCE: 20
```

-continued

```
aaaggtgtcc agtgtcagca gcagctggtg gagtccgggg gaggcctggt caagcctggg     60
gcatccctga cactcacctg cacagcctct ggattctcct tcagtagcgg cagcgacatg    120
tgctgggtcc gccagcctcc agggaagggg ctggagtgga tcgcatgcat tggcattagt    180
agtggtagca cttactacgc gaactgggcg aaaggccgat tcaccatctc caaaacctcg    240
tcgaccacgg tgactctgca aatgaccagt ctgacagccg cggacacggc cacctatttc    300
tgtgcgagag ctatagggcc tttccacttt aacttgtggg gccaggcac cctggtcacc      360 gtctcctcag ggcaacctaa ggctccatca gtcttccac tggccccctg ctgcgggg       418
```

<210> SEQ ID NO 21
<211> LENGTH: 373
<212> TYPE: DNA
<213> ORGANISM: Artificial Sequence
<220> FEATURE:
<223> OTHER INFORMATION: Synthetic construct

<400> SEQUENCE: 21

```
gctcccaggt gccacatttg ccatcgtgat gacccagact ccatcttcca agtctgtccc     60
tgtgggagac acagtcacca tcaattgcca ggccagtgag agtgtttata gtaacaaccg    120
cttagcctgg tatcagcaga aaccagggca gcctcccaag ctcctgatct atggtgcatc    180
cactctggca tctggggtcc catcgcggtt caaaggcagc ggatctggga cacagttcac    240
tctcaccatc agcgatgtgg tgtgtgacga tgctgccact tactactgtg caggatataa    300
aagtggtatt ggtgatggta ttgctttcgg cggagggacc gaggtggtgg tcaaaggtga    360
tccagttgca cct                                                        373
```

<210> SEQ ID NO 22
<211> LENGTH: 415
<212> TYPE: DNA
<213> ORGANISM: Artificial Sequence
<220> FEATURE:
<223> OTHER INFORMATION: Synthetic construct

<400> SEQUENCE: 22

```
aaaggtgtcc agtgtcagtc gttggaggag tccgggggag acctggtcaa gcctgaggga     60
tccctgacac tcacctgcac agcttctgga ttctccttca gtaccaacta cgacatgtgc    120
tgggtccgcc aggctccagg gaaggggctg agtggatcg catgcgttgg tgctggtagt     180
ggtagcactt actacgcgag ctgggcgaaa ggccggttca ccatctccaa aacctcgtcg    240
accacggtga ctctgcaaat gaccagtctg acagccgcgg acacggccac ctatttctgt    300
gcgagatgga ctagtggtct ttatattaac ttctggggcc aggcaccct ggtcaccgtc      360 tcctcagggc aacctaaggc tccatcagtc ttcccactgg cccctgctg cgggg          415
```

<210> SEQ ID NO 23
<211> LENGTH: 373
<212> TYPE: DNA
<213> ORGANISM: Artificial Sequence
<220> FEATURE:
<223> OTHER INFORMATION: Synthetic construct

<400> SEQUENCE: 23

```
gctcccaggt gccacatttg ccatcgtgat gacccagact ccatcttcca agtctgtccc     60
tgtgggagac acagtcacca tcaattgcca ggccagtgag agtgtttata gtaacaaccg    120
cttagcctgg tttcaacaga aaccagggca gcctcccaag ctcctgatct atctggcatc    180
```

-continued

```
cactctggca tctggggtcc catcgcggtt caaaggcagt ggatctggga cacagttcac      240
tctcaccatc agcgatgtgg tgtgtgacga tgctgccact tactactgta caggatataa      300
aagtagtaat actgatggta tcggtttcgg cggagggacc gaggtggtgg tcaaaggtga      360
tccagttgca cct                                                        373

<210> SEQ ID NO 24
<211> LENGTH: 373
<212> TYPE: DNA
<213> ORGANISM: Artificial Sequence
<220> FEATURE:
<223> OTHER INFORMATION: Synthetic construct

<400> SEQUENCE: 24
gctcccaggt gccacatttg ccatcgtgat gacccagact ccatcttcca agtctgtccc       60
tgtgggagac acagtcacca tcagttgcca ggccagtgag agtgtttata gtaacaaccg      120
cttagcctgg tttcaacaga aaccagggca gcctcccaag ctcctgatct atctggcatc      180
cactctggca tctggggtcc catcgcggtt caaaggcagt ggatctggga cacagttcac      240
tctcaccatc agcgatgtgg tgtgtgacga tgctgccact tactactgtg caggatataa      300
aattagtaat actgatggta tcggtttcgg cggagggacc gaggtggtgg tcaaaggtga      360
tccagttgca cct                                                        373

<210> SEQ ID NO 25
<211> LENGTH: 418
<212> TYPE: DNA
<213> ORGANISM: Artificial Sequence
<220> FEATURE:
<223> OTHER INFORMATION: Synthetic construct

<400> SEQUENCE: 25
aaaggtgtcc agtgtcagca gcagctggtg gagtccgggg gaggcctggt caagcctggg       60
gcatccctga cactcacctg caaagcctct agattctcct tcagtagcgc ctacgacatg      120
ggctgggtcc gccaggctcc agggaagggg ctggagtgga tcgcatgcat tggtagtagt      180
agtggtacca cttactacgc gagctgggcg aaaggccgat tcaccatctc caaaacctcg      240
tcgaccacgg tgactctgca aatgaccagt ctgacagccg cggacacggc cacctatttc      300
tgtgcgagag cgcagtcccc cttccacttt aacttgtggg gccaggcac cctggtcgcc      360 gtctcctcag ggcaacctaa ggctccatca gtcttccac tggcccctg ctgcgggg       418

<210> SEQ ID NO 26
<211> LENGTH: 373
<212> TYPE: DNA
<213> ORGANISM: Artificial Sequence
<220> FEATURE:
<223> OTHER INFORMATION: Synthetic construct

<400> SEQUENCE: 26
gctcccaggt gccacatttg ccatcgtgat gacccagact ccatcttcca agtctgtccc       60
tgtgggagac acagtcacca tcaattgcca ggccagtgag agtgtttata gtaacaaccg      120
cttagcctgg tatcaacaga aaccagggca gcctcccaag ctcctgatct atggtgcatc      180
cactctggca tctggggtcc catcgcggtt caaaggcagt ggatctggga cacagttcac      240
tctcaccatc agcgatgtgg tgtgtgacga tgctgccact tactactgtg caggatataa      300
aagtagtagt actgatggtt ttgctttcgg cggagggacc gaggtggtgg tcaaaggtga      360
tccagttgca cct                                                        373
```

```
<210> SEQ ID NO 27
<211> LENGTH: 418
<212> TYPE: DNA
<213> ORGANISM: Artificial Sequence
<220> FEATURE:
<223> OTHER INFORMATION: Synthetic construct

<400> SEQUENCE: 27
aaaggtgtcc agtgtcagca gcagctggtg gagtccgggg gaggcctggt caagcctggg     60
gcatccctga cactcacctg cacagcctct ggattctcct tcagtagata cagcgacatg    120
tgctgggtcc gccagcctcc agggaagggg ctggagtgga tcgcatgtat tggcattagt    180
agtggtacca cttactacgc gagctgggcg aaaggccgat tcaccatctc caaaacctcg    240
tcgaccacgg tgactctgca aatgaccagt ctgacagccg cggacacggc cacctatttg    300
tgtacgagag ctatcgggcc tttccacttt aatttgtggg gcccaggcac cctggtcacc    360
gtctcctcag ggcaacctaa ggctccatca gtcttccac tggcccctg ctgcgggg      418

<210> SEQ ID NO 28
<211> LENGTH: 373
<212> TYPE: DNA
<213> ORGANISM: Artificial Sequence
<220> FEATURE:
<223> OTHER INFORMATION: Synthetic construct

<400> SEQUENCE: 28
gctcccaggt gccacatttg ccatcgtgat gacccagact ccatcttcca ggtctgtccc     60
tgtgggagac acagtcacca tcagttgcca ggccagtgag agtgtttata ataacaaccg    120
cttagcctgg tatcagcaga aagcaggaca gcctcccaag ctcctgatct atggtgcatc    180
cactctggca tctggggtcc catcgcggtt caaaggcagc ggatctggga cacagttcac    240
tctcaccatc agcgatgtgg tgtgtgacga tgctgccact tactactgtg caggatataa    300
aagtggtagt actgatggtt gtgctttcgg cggagggacc gaggtggtgg tcaaaggtga    360
tccagttgca cct                                                      373

<210> SEQ ID NO 29
<211> LENGTH: 418
<212> TYPE: DNA
<213> ORGANISM: Artificial Sequence
<220> FEATURE:
<223> OTHER INFORMATION: Synthetic construct

<400> SEQUENCE: 29
aaaggtgtcc agtgtcagca gcagctggtg gagtccgggg gaggcctggt caagcctggg     60
gcatccctga cactcacctg cacagcctct ggattctcct tcagtaggga cagcgacatg    120
tgctgggtcc gccagcctcc agggaagggg ctggagtgga tcgcatgtat tggcattagt    180
agtggtatca cttactacgc gaactgggcg agaggccgat tcaccatctc caaaacctcg    240
tcgaccacgg tgactctgca aatgaccagt ctgacagccg cggacacggc cacctatttc    300
tgtgcgagag ctatagggcc tttccacttt aacttgtggg gcccaggcac cctggtcacc    360
gtctcctcag ggcaacctaa ggctccatca gtcttcccac tggccccctg ctgcgggg      418

<210> SEQ ID NO 30
<211> LENGTH: 373
<212> TYPE: DNA
<213> ORGANISM: Artificial Sequence
<220> FEATURE:
```

-continued

<223> OTHER INFORMATION: Synthetic construct

<400> SEQUENCE: 30

```
gctcccaggt gccacatttg ccatcgtgat gacccagact ccatcttcca agtctgtccc       60
tgtgggagac acagtcacca tcgattgcca ggccagtgag agtgtttata gtaagaaccg      120
cttagcctgg taccagcaga aaccagggca gcctcccaag ctcctgatct atggtgcatc      180
cactctggca tctggggtcc catcgcggtt caaaggcagc ggatctggga cacagttcac      240
tctcaccgtc agcgatgtgg tgtgtgacga tgctgccact tactactgtg caggatataa      300
aagtggtatt ggtgatggta ttgctttcgg cggagggacc gaggtggtgg tcaaaggtga      360
tccagttgca cct                                                        373
```

<210> SEQ ID NO 31
<211> LENGTH: 42
<212> TYPE: PRT
<213> ORGANISM: Homo sapiens

<400> SEQUENCE: 31

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 32
<211> LENGTH: 139
<212> TYPE: PRT
<213> ORGANISM: Artificial Sequence
<220> FEATURE:
<223> OTHER INFORMATION: Synthetic construct

<400> SEQUENCE: 32

```
Lys Gly Val Gln Cys Gln Gln Gln Leu Val Glu Ser Gly Gly Gly Leu
1               5                   10                  15

Val Lys Pro Gly Ala Ser Leu Thr Leu Thr Cys Lys Ala Ser Gly Phe
            20                  25                  30

Ser Phe Ser Ser Ala Tyr Asp Met Cys Trp Val Arg Gln Ala Pro Gly
        35                  40                  45

Lys Gly Leu Glu Trp Ile Ala Cys Ile Gly Cys Ser Ser Gly Thr Thr
    50                  55                  60

Tyr Tyr Ala Thr Trp Ala Lys Gly Arg Phe Thr Ile Ser Lys Thr Ser
65                  70                  75                  80

Ser Thr Thr Val Thr Leu Gln Met Thr Ser Leu Thr Ala Ala Asp Thr
                85                  90                  95

Ala Thr Tyr Phe Ser Ala Arg Ala Gln Ser Pro Phe His Phe Asn Leu
            100                 105                 110

Trp Gly Pro Gly Thr Leu Val Ala Val Ser Ser Gly Gln Pro Lys Ala
        115                 120                 125

Pro Ser Val Phe Pro Leu Ala Pro Cys Cys Gly
    130                 135
```

<210> SEQ ID NO 33
<211> LENGTH: 124
<212> TYPE: PRT
<213> ORGANISM: Artificial Sequence
<220> FEATURE:
<223> OTHER INFORMATION: Synthetic construct -continued

```
<400> SEQUENCE: 33

Leu Pro Gly Ala Thr Phe Ala Ile Val Met Thr Gln Thr Pro Ser Ser
1               5                   10                  15

Lys Ser Val Pro Val Gly Asp Thr Val Thr Ile Asn Cys Gln Ala Ser
            20                  25                  30

Glu Ser Val Tyr Ser Asn Asn Arg Leu Ala Trp Tyr Gln Gln Lys Pro
        35                  40                  45

Gly Gln Pro Pro Lys Leu Leu Ile Tyr Gly Ala Ser Thr Leu Ala Ser
    50                  55                  60

Gly Val Pro Ser Arg Phe Lys Gly Ser Gly Ser Gly Thr Gln Phe Thr
65                  70                  75                  80

Leu Thr Ile Ser Asp Val Val Cys Asp Asp Ala Ala Thr Tyr Tyr Cys
                85                  90                  95

Ala Gly Tyr Lys Ser Ser Thr Thr Asp Gly Phe Ala Phe Gly Gly Gly
            100                 105                 110

Thr Glu Val Val Val Lys Gly Asp Pro Val Ala Pro
        115                 120

<210> SEQ ID NO 34
<211> LENGTH: 137
<212> TYPE: PRT
<213> ORGANISM: Artificial Sequence
<220> FEATURE:
<223> OTHER INFORMATION: Synthetic construct

<400> SEQUENCE: 34

Lys Gly Val Gln Cys Gln Ser Leu Glu Glu Ser Gly Gly Asp Leu Val
1               5                   10                  15

Lys Pro Glu Gly Ser Leu Thr Leu Thr Cys Thr Ala Ser Gly Phe Ser
            20                  25                  30

Phe Ser Ser Asn Tyr Asp Met Cys Trp Val Arg Gln Ala Pro Gly Lys
        35                  40                  45

Gly Leu Gln Trp Ile Ala Cys Val Gly Asp Ser Gly His Thr Tyr Tyr
    50                  55                  60

Ala Ser Trp Ala Lys Gly Arg Phe Thr Ile Ser Lys Thr Ser Ser Thr
65                  70                  75                  80

Thr Val Thr Leu Gln Met Thr Ser Leu Thr Ala Ala Asp Thr Ala Thr
                85                  90                  95

Tyr Phe Cys Ala Arg Trp Thr Ser Gly Leu Tyr Ile Asn Phe Trp Gly
            100                 105                 110

Pro Gly Thr Leu Val Thr Val Ser Ser Gly Gln Pro Lys Ala Pro Ser
        115                 120                 125

Val Phe Pro Leu Ala Pro Cys Cys Gly
    130                 135

<210> SEQ ID NO 35
<211> LENGTH: 418
<212> TYPE: DNA
<213> ORGANISM: Artificial Sequence
<220> FEATURE:
<223> OTHER INFORMATION: Synthetic construct

<400> SEQUENCE: 35
aaaggtgtcc agtgtcagca gcagctggtg gagtccgggg gaggcctggt caagcctggg      60
gcatccctga cactcacctg caaagcctct ggattctcct tcagtagcgc ctacgacatg     120
tgctgggtcc gccaggctcc agggaagggg ctggagtgga tcgcatgcat tggttgtagt     180
```

-continued

```
agtggtacca cttactatgc gacctgggcg aaaggccgat tcaccatctc caaaacctcg    240
tcgaccacgg tgactctgca aatgaccagt ctgacagccg cggacacggc cacgtatttc    300
tctgcgagag cgcagtcccc cttccacttt aacttgtggg gcccaggcac cctggtcgcc    360
gtctcctcag ggcaacctaa ggctccatca gtcttccac tggccccctg ctgcgggg      418

<210> SEQ ID NO 36
<211> LENGTH: 373
<212> TYPE: DNA
<213> ORGANISM: Artificial Sequence
<220> FEATURE:
<223> OTHER INFORMATION: Synthetic construct

<400> SEQUENCE: 36
gctcccaggt gccacatttg ccatcgtgat gacccagact ccatcttcca agtctgtccc     60
tgtgggagac acagtcacca tcaattgcca ggccagtgag agtgtttata gtaacaaccg    120
cttagcctgg tatcagcaga aaccagggca gcctcccaag ctcctgatct atggtgcatc    180
cactctggca tctggggtcc catcgcggtt caaaggcagt ggatctggga cacagttcac    240
tctcaccatc agcgatgtgg tgtgtgacga tgctgccact tactactgtg caggatacaa    300
aagtagtact actgatggtt ttgctttcgg cggagggacc gaggtggtgg tcaaaggtga    360
tccagttgca cct                                                       373

<210> SEQ ID NO 37
<211> LENGTH: 412
<212> TYPE: DNA
<213> ORGANISM: Artificial Sequence
<220> FEATURE:
<223> OTHER INFORMATION: Synthetic construct

<400> SEQUENCE: 37
aaaggtgtcc agtgtcagtc gttggaggag tccgggggag acctggtcaa gcctgaggga     60
tccctgacac tcacctgcac agcttctgga ttctccttca gtagcaacta cgacatgtgc    120
tgggtccgcc aggctccagg gaaggggctg cagtggatcg catgcgttgg tgatagtggt    180
catacttact acgcgagctg ggcgaaaggc cggttcacca tctccaaaac ctcgtcgacc    240
acggtgactc tgcaaatgac cagtctgaca gccgcggaca cggccaccta tttctgtgcg    300
agatggacta gtggtcttta tattaatttt tggggcccag gcaccctggt caccgtctcc    360
tcagggcaac ctaaggctcc atcagtcttc ccactggccc cctgctgcgg gg           412
```